(12) United States Patent
Rizoiu et al.

(10) Patent No.: US 7,467,946 B2
(45) Date of Patent: Dec. 23, 2008

(54) ELECTROMAGNETIC RADIATION EMITTING TOOTHBRUSH AND DENTIFRICE SYSTEM

(75) Inventors: Ioana M. Rizoiu, San Clemente, CA (US); Jeffrey W. Jones, Robertson, WY (US); Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 204 days.

(21) Appl. No.: 11/438,091

(22) Filed: May 18, 2006

(65) Prior Publication Data
US 2006/0281042 A1 Dec. 14, 2006

Related U.S. Application Data

(60) Provisional application No. 60/739,314, filed on Nov. 23, 2005, provisional application No. 60/688,109, filed on Jun. 6, 2005, provisional application No. 60/682,752, filed on May 18, 2005.

(51) Int. Cl.
*A61C 17/22* (2006.01)
(52) U.S. Cl. .......................... 433/29; 433/80
(58) Field of Classification Search .................. 433/29; 215/22.1, 105, 167.1; 15/22.1, 105, 167.1
See application file for complete search history.

(56) References Cited

U.S. PATENT DOCUMENTS

| | | | |
|---|---|---|---|
| 2,834,344 A | 5/1958 | Kanai | |
| 3,261,978 A | 7/1966 | Brenman | |
| 3,478,741 A | 11/1969 | Simor | |
| 3,520,297 A | 7/1970 | Bechtold | |
| 4,273,535 A | 6/1981 | Yamamoto et al. | |
| 4,502,497 A | 3/1985 | Siahou | |
| 4,661,070 A | 4/1987 | Friedman | |
| 4,779,173 A | 10/1988 | Carr et al. | |
| 4,877,401 A | 10/1989 | Higuchi et al. | |
| 4,890,732 A * | 1/1990 | Shackelford | 206/362.1 |
| 4,952,143 A | 8/1990 | Becker et al. | |
| 4,969,868 A | 11/1990 | Wang | |
| 4,983,381 A | 1/1991 | Torres Zaragoza | |

(Continued)

FOREIGN PATENT DOCUMENTS

EP 0 406 454 1/1991

(Continued)

OTHER PUBLICATIONS

International Preliminary Examination Report, Mar. 15, 2000, PCT/US98/12836.

(Continued)

*Primary Examiner*—Ralph A Lewis
(74) *Attorney, Agent, or Firm*—Stout, Uxa, Buyan & Mullins, LLP

(57) ABSTRACT

A device includes a handle coupled with an activated textured surface that can be implemented using a repetitive movement mechanism and a treatment energy source, such as an electromagnetic radiation source. The handle may be used to provide detection, treatment and/or management of sundry conditions including, for example, tooth discoloration, tissue damage, periodontal disease, tumors, pain, halitosis, and bronchitis. The activated textured surface may include a surface topography including corrugations, bristles, protuberances, or pits, or other surfaces for facilitating agitation, cleaning or other surface treatments.

34 Claims, 9 Drawing Sheets

U.S. PATENT DOCUMENTS

| | | |
|---|---|---|
| 5,003,434 A | 3/1991 | Gonser et al. |
| 5,030,090 A | 7/1991 | Maede et al. |
| 5,030,093 A | 7/1991 | Mitnick |
| 5,032,178 A | 7/1991 | Cornell |
| 5,055,048 A | 10/1991 | Vassiliadis et al. |
| 5,094,619 A | 3/1992 | McLaughlin |
| 5,160,194 A | 11/1992 | Feldman |
| 5,306,143 A | 4/1994 | Levy |
| 5,611,793 A | 3/1997 | Wilson et al. |
| 5,658,148 A | 8/1997 | Neuberger et al. |
| 6,089,740 A | 7/2000 | Forehand et al. |
| 6,202,242 B1 | 3/2001 | Salmon et al. |
| 6,616,451 B1 | 9/2003 | Rizoiu et al. |
| 6,685,471 B1 * | 2/2004 | Kawamura et al. ............ 433/29 |
| 6,832,771 B2 | 3/2005 | Muller |
| 2003/0232303 A1 | 12/2003 | Black |
| 2004/0006332 A1 | 1/2004 | Black |
| 2004/0091834 A1 | 5/2004 | Rizoiu et al. |
| 2004/0191729 A1 | 9/2004 | Altshuler et al. |
| 2004/0193235 A1 | 9/2004 | Altshuler et al. |
| 2004/0193236 A1 | 9/2004 | Altshuler et al. |
| 2004/0204745 A1 | 10/2004 | Altshuler et al. |
| 2004/0210276 A1 | 10/2004 | Altshuler et al. |
| 2005/0050658 A1 | 3/2005 | Chan et al. |
| 2005/0050659 A1 | 3/2005 | Chan et al. |
| 2005/0052895 A1 | 3/2005 | Pinyayev et al. |
| 2005/0052896 A1 | 3/2005 | Pinyayev et al. |
| 2005/0053898 A1 | 3/2005 | Ghosh et al. |
| 2005/0066459 A1 * | 3/2005 | Pinyayev et al. ............... 15/28 |
| 2006/0183071 A1 * | 8/2006 | Hsuch ......................... 433/29 |

FOREIGN PATENT DOCUMENTS

| | | |
|---|---|---|
| WO | WO/92/06671 | 4/1992 |
| WO | WO/93/09847 | 5/1993 |
| WO | WO/94/19850 A | 5/1994 |
| WO | WO/97/01298 | 1/1997 |
| WO | WO/98/10711 A | 3/1998 |

OTHER PUBLICATIONS

International Search Report, Dec. 30, 1998, PCT/US98/12836.
European Search Report, Jul. 15, 2005, EP 98 93 1410.

* cited by examiner

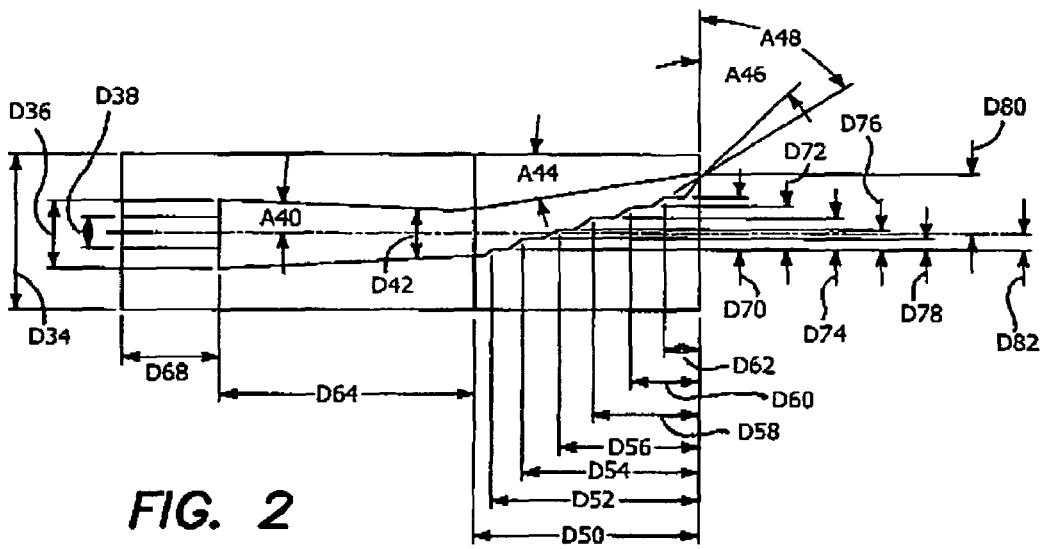
FIG. 2
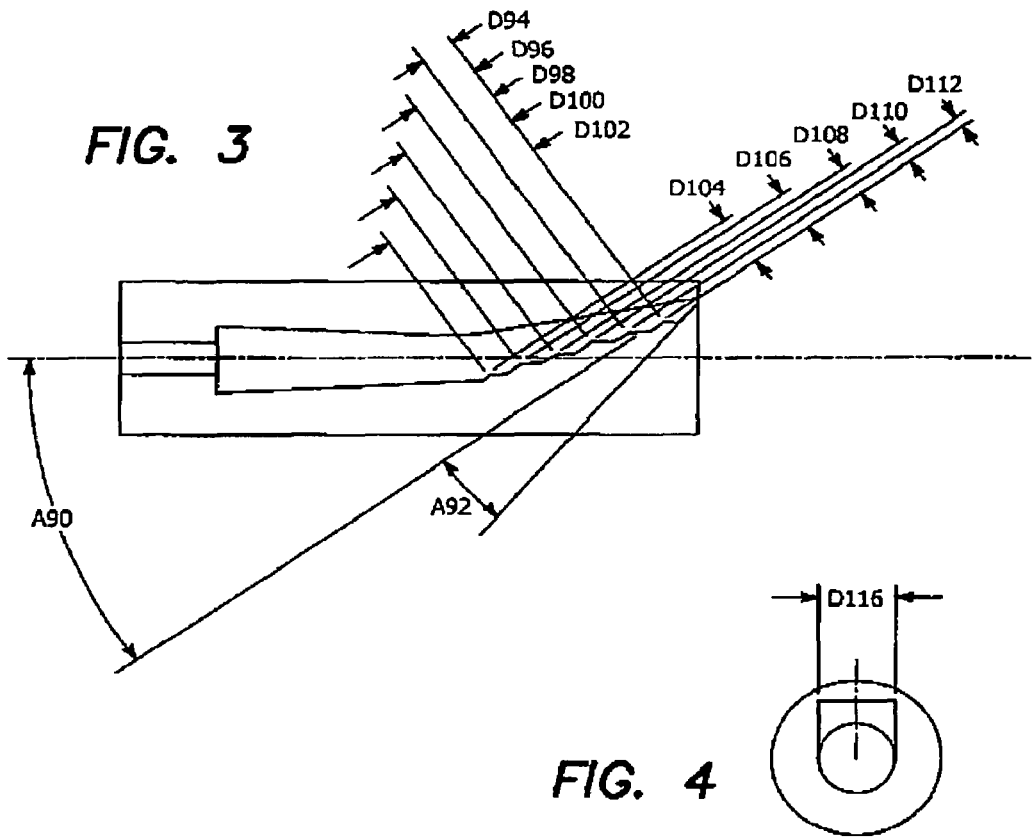
FIG. 3
FIG. 4

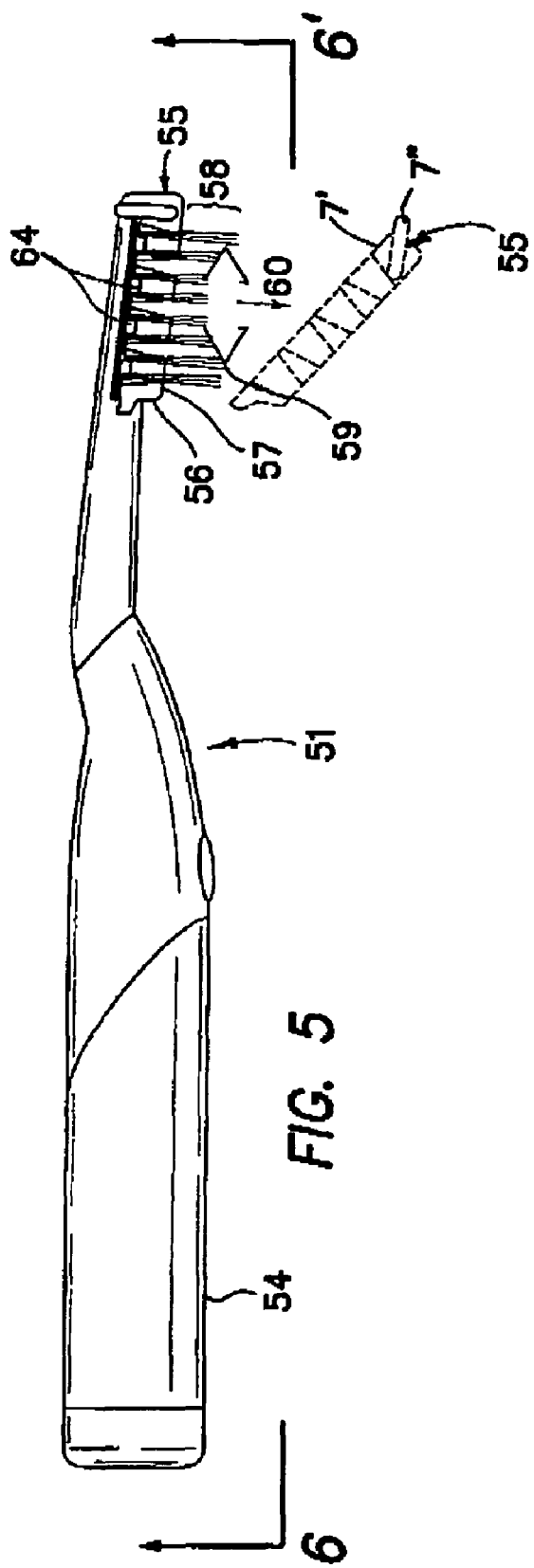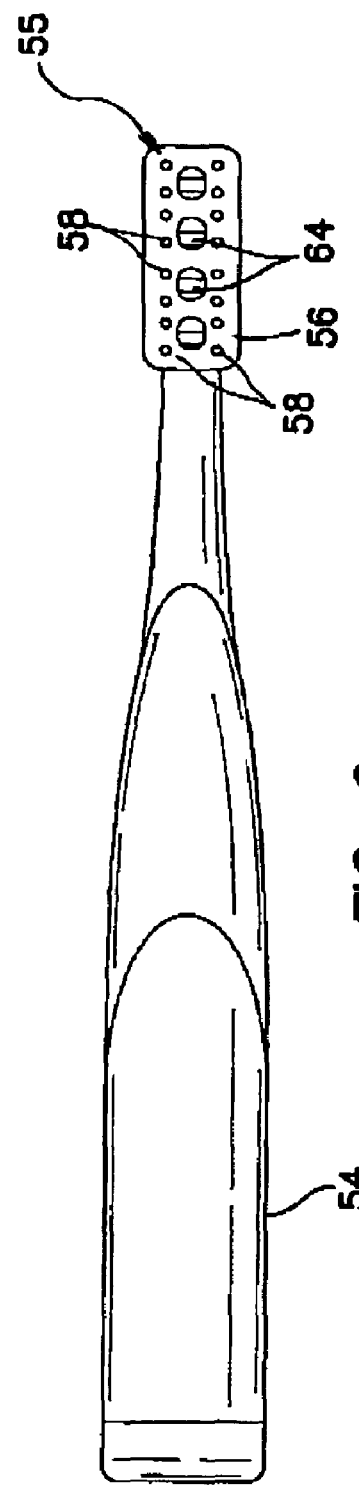

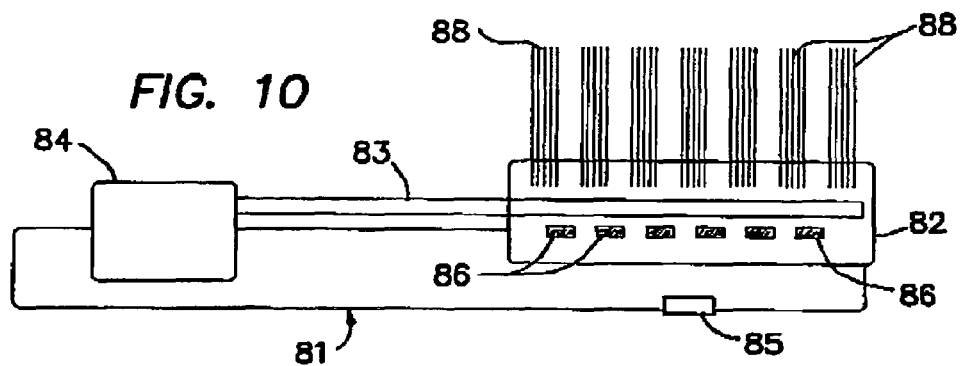
FIG. 10
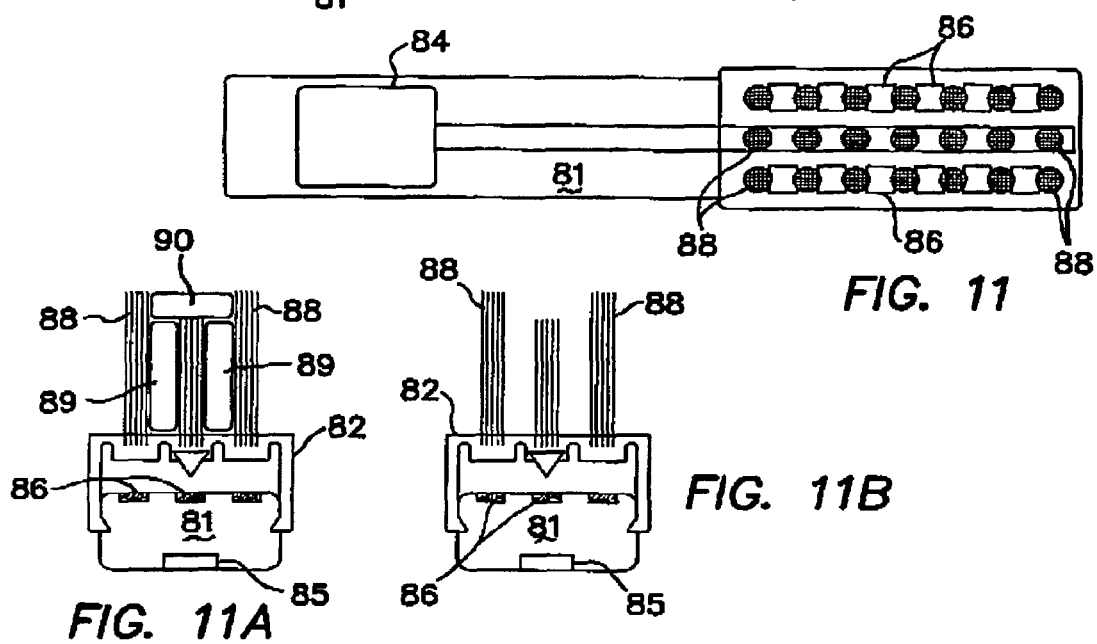
FIG. 11
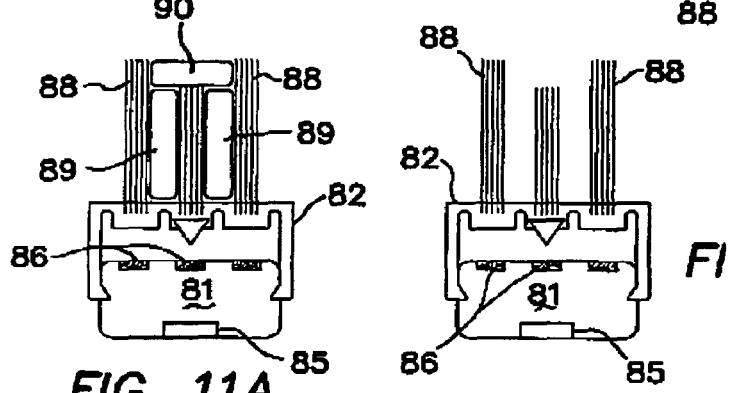
FIG. 11A
FIG. 11B
FIG. 11C
FIG. 11D
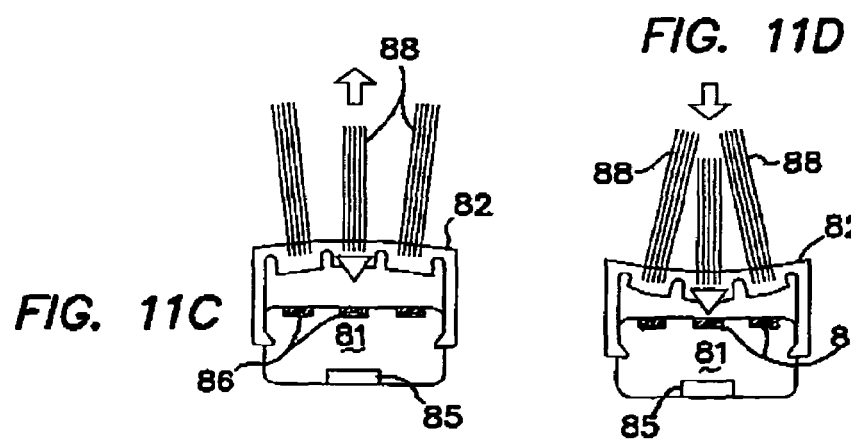
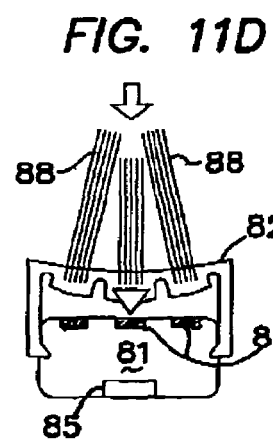

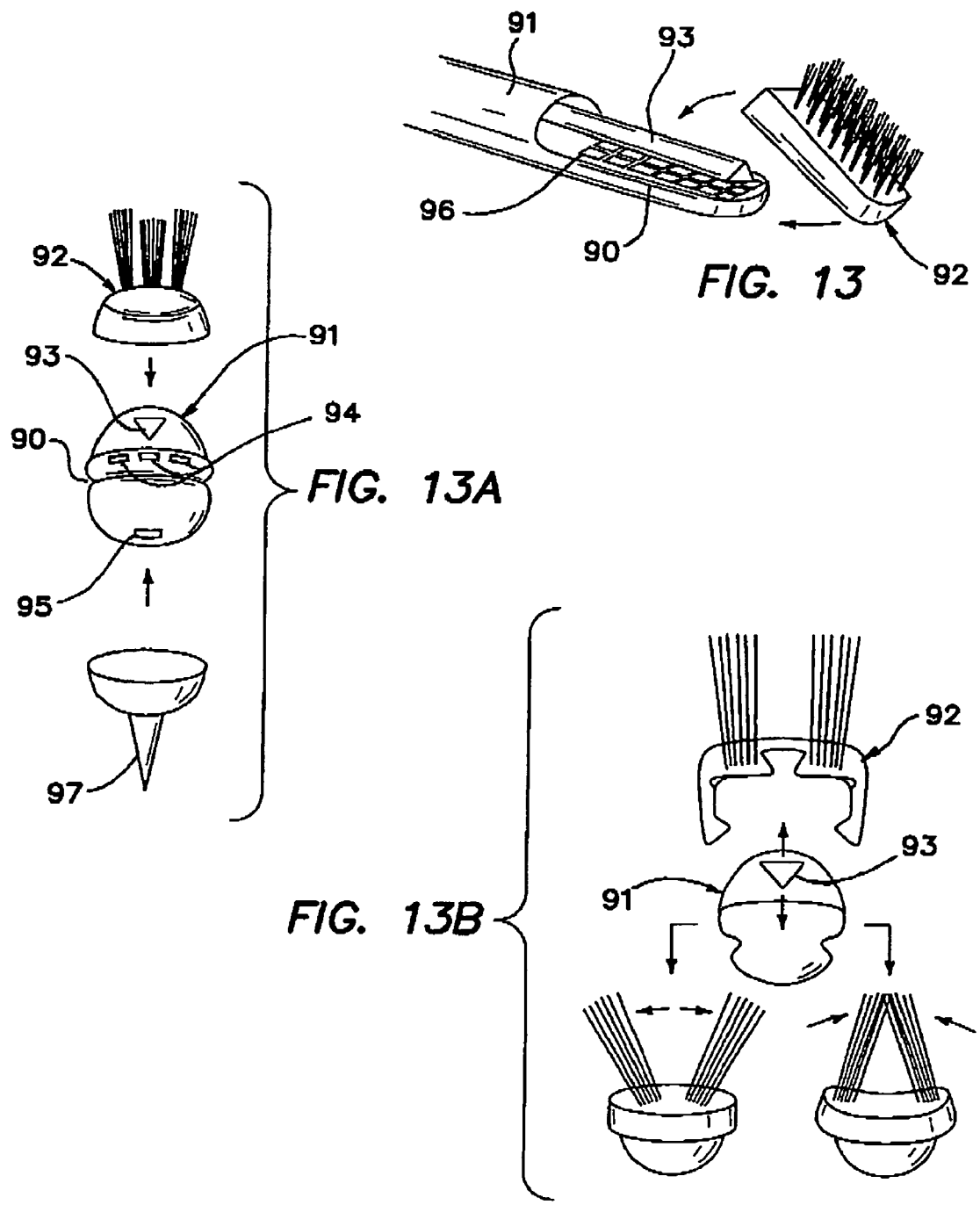

ELECTROMAGNETIC RADIATION EMITTING TOOTHBRUSH AND DENTIFRICE SYSTEM

CROSS-REFERENCE TO RELATED APPLICATIONS

This application claims the benefit of U.S. Provisional Application No. 60/682,752, filed May 18, 2005, U.S. Provisional Application No. 60/688,109, filed Jun. 6, 2005 and U.S. Provisional Application No. 60/739,314, filed Nov. 23, 2005, the entire contents of which are hereby incorporated by reference.

This application is related to U.S. Pat. No. 6,616,451, which issued on Sep. 9, 2003 and which claims the benefit of U.S. Provisional Application No. 60/050,343, filed on Jun. 20, 1997 and entitled ELECTROMAGNETIC RADIATION EMITTING TOOTHBRUSH AND TRANSPARENT TOOTHPASTE COMBINATION, the entire contents of both which are expressly incorporated herein by reference. This application is also related to U.S. application Ser. No. 11/074,452, filed Mar. 8, 2005 and entitled RADIATION EMMITTING APPARATUS WITH SPATIALLY CONTROLLABLE OUTPUT ENERGY DISTRIBUTIONS, which is a continuation of U.S. application Ser. No. 10/229,374, filed Aug. 26, 2002 and entitled RADIATION EMMITTING APPARATUS WITH SPATIALLY CONTROLLABLE OUTPUT ENERGY DISTRIBUTIONS, the entire contents of all which are hereby incorporated by reference. This application further is related to U.S. Pat. No. 6,616,447, which issued on Sep. 9, 2003 and which claims the benefit of U.S. Provisional Application No. 60/249,015, filed Nov. 15, 2000 and entitled DEVICE FOR DENTAL CARE AND WHITENING, the entire contents of both which are hereby incorporated by reference.

BACKGROUND OF THE INVENTION

Various toothbrushes have existed in the prior art, including toothbrushes having light-emitting elements, automated moving and cleaning implements, and combinations of these elements and implements.

SUMMARY OF THE INVENTION

A device includes a handle coupled with an activated textured surface that can be implemented using a repetitive movement mechanism and a treatment energy source, such as an electromagnetic radiation source. The handle may be used to provide detection, treatment and/or management of sundry conditions including, for example, tooth discoloration, tissue damage, periodontal disease, tumors, pain, halitosis, and bronchitis. The activated textured surface may include a surface topography including corrugations, bristles, protuberances, or pits, or other surfaces for facilitating agitation, cleaning or other surface treatments.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE DRAWINGS

FIGS. 2-4 are schematic views of an electromagnetic radiation emitting toothbrush according to another embodiment of the invention;

FIG. 5 is a side elevation view of another electromagnetic radiation emitting toothbrush according to an embodiment of the invention;

FIG. 6 is a top planar of the other electromagnetic radiation emitting toothbrush shown from a perspective of the line 6-6' of FIG. 5;

FIGS. 7-18 depict additional embodiments of the present invention.

DETAILED DESCRIPTION OF THE PRESENT INVENTION

Figure 1:
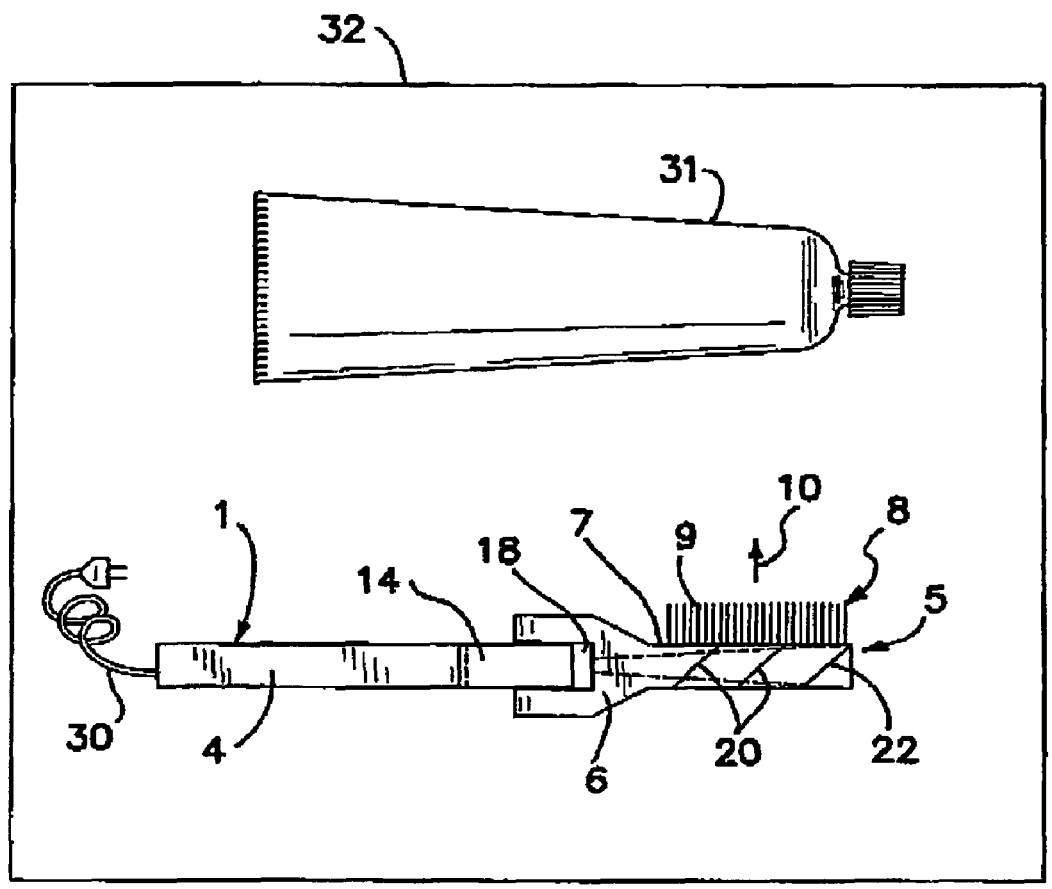
FIG. 1 is a schematic view of an electromagnetic radiation emitting toothbrush and a container of brushing compound in a package according to an embodiment of the invention.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the claims. It is to be understood and appreciated that the process steps and structures described or incorporated by reference herein do not cover a complete process flow for the implementations described herein. The present invention may be practiced in conjunction with various medical devices that are conventionally used in the art, and only so much of the commonly practiced method steps are included herein as are necessary to provide an understanding of the present invention.

Any feature or combination of features described herein are included within the scope of the present invention provided that the features included in any such combination are not mutually inconsistent as will be apparent from the context, this specification, and the knowledge of one of ordinary skill in the art.

Although the disclosure herein refers to the use of a device having activated textured surfaces (e.g., lighted with bristles) for treating tissue (e.g., teeth) surfaces of the oral cavity, the device and process of the present invention are not limited to such uses. Devices of the present invention may be used, or modified for use, for any medical purpose that may benefit from the application of automated movement of textured surfaces on or within tissues of the body.

The device of the present invention generally can include a handle coupled with an activated textured surface that can be implemented using one or more of, for example, a repetitive movement mechanism and a treatment energy source (e.g., an electromagnetic radiation source).

The handle may be used to provide detection, treatment and/or management of sundry conditions including, for example, tooth discoloration, tissue damage, periodontal disease, tumors, pain, halitosis, and bronchitis.

The activated textured surface may include a surface topography comprising one or more of corrugations, bristles, protuberances, pits, other surfaces known to those skilled in the art to be suitable for facilitating agitation, cleaning or other surface treatments, and combinations thereof. Surface topographies of or analogous to one or more of sponges, fabrics, brushes, steel wool, toothbrushes, other cleaning or wiping surfaces, and combinations thereof, may be implemented using various known materials. For example, surface topographies of household cleaning, wiping, or scrubbing pads comprising, for example, one or more of rayon/polypropylene fabrics or sponges, polyester fabrics and polyester knits may be implemented using the same or different materials. Textured surfaces may comprise, as other examples, silicon or rubber base materials with surface topographies defined by one or more of plastic, silicon, hardened durometer rubber or stainless steel protuberances or indentations.

The repetitive movement mechanism may comprise one or more of manual (e.g., powered by movement of a user) and electric movement mechanisms and further may comprise one or more of a surface disrupting mechanism, a mechanical movement mechanism (e.g., (cam, linkage system, off-center mass), other implementations for activating (e.g., facilitating repetitive movement of) the textured surface (e.g., by way of acoustic (e.g., ultrasonic), piezo-ceramic or other elements or generators), and combinations thereof. In certain embodiments, the textured surface can be activated using, for example, oscillating or acoustic (e.g., ultrasonic) motion by way of, for example, motorized or vibrating devices. Motorized devices may comprise, for example, electromechanical devices powered by batteries or power chords, and vibrating devices may comprise, for example, water-powered or piezo-electric implementations formed on or within the handle. In modified embodiments, power requirement of any component described or implicitly/inherently disclosed herein, may be supplied or met, partially or fully, by way of a kinetic motion power generator (such as found in, for example, wrist watches) coupled or disposed within the handle (e.g., when the handle comprises a toothbrush, brushing movement of the toothbrush may be converted into power) by the kinetic motion power generator. In other embodiments, movement from an external source, such as a hand of a user or other implementation, can alternatively or additionally facilitate (e.g., transfer) movement of or to the textured surface.

A treatment energy source (e.g., electromagnetic radiation source) may be used, solely or in combination with a movement mechanism, to activate the textured surface. The treatment energy source (e.g., electromagnetic radiation source) may comprise any known implementation for emitting treatment doses of electromagnetic energy toward one or more of the textured surface and the tissue surface. According to one embodiment, the electromagnetic energy may be delivered, in whole or in part, as magnetism (e.g., from magnets within, or electrically activated within, the handle) for implementing, for example, magnetic therapy. According to another embodiment, the electromagnetic energy may be delivered, in whole or in part, as heat (e.g., ultraviolet light and/or radiation from a heating element).

As used herein, the term "treatment doses" is intended to refer to quantities and concentrations of electromagnetic energy that are sufficient to effectuate desired chemical (e.g., enhancing a reaction time) or other (e.g., ablation) reactions on the textured surface or tissue surface and/or to cause one or more therapeutic or other intended effects (e.g., greater circulation or pain reduction) on or in the tissue of the tissue surface.

In certain implementations, low-level light therapy (LLLT) may be beneficially applied to tissues using (e.g., via light transmitted from) the handle. Treatment power densities may be relatively low, being similar, for example, to power densities used in treatments of, e.g., tennis elbow, temporomandibular joint (TMJ), or tendonitis, and in representative embodiments having characteristics less than the following: a power density at the surface of the tissue being treated of about 1.47 $W/cm^2$, a power density within the tissue of about 0.39 $W/cm^2$, a dose of energy of about 23.6 $J/cm^2$ (for a 60 second laser exposure), and/or an energy of about 9 J within and about 33.5 J at the surface of the tissue being treated. The LLLT may originate from a treatment energy source (e.g., electromagnetic radiation source) disposed on or within the handle as described herein and/or disposed separate and apart from the handle, and may be implemented continuously or at predetermined periods of time (e.g., at times when an orthodontic structure, such as braces, is tightened) for predetermined durations.

Examples of virus combating (e.g., destroying) treatment energies can comprise electromagnetic radiation sources, such as diode lasers having wavelengths ranging from about 810 nm to about 980 nm, Nd:YAG lasers having wavelengths ranging from about 1060 to about 3200 nm, $CO_2$ lasers having wavelengths of about 10600, and Er type lasers having wavelengths ranging from about is 2780 to about 2940 nm. In other embodiments, other wavelengths can be used, for example, for thermally destroying viruses to the extent care is taken not to scar or thermally damage adjacent areas. For instance, aphtous ulcers can be treated with, for example, Nd:YAG or diode lasers at relatively low energy (e.g., an average power of about 1 W and a spot size of about 400 to 800 microns) settings. Such electromagnetic radiation can be applied to a treatment area for about a minute, followed by allowing the area to thermally relax and determining whether any pain is felt by the patient, followed by the process being repeated if, for example, pain continues to be experienced by the patient, for up to about 6 treatment cycles.

According to embodiments wherein a dentifrice is used in combination with the treatment energy source (e.g., an electromagnetic radiation source), the dentifrice may comprise, for example, a reactive agent (e.g., a peroxy compound), and a wavelength of the treatment energy source may be selected to correspond to that agent in order to effectuate a desired reaction or result (e.g., enhanced tooth whitening). In one embodiment, the electromagnetic radiation source is selected to emit green light, which has been found by the present inventors to potentially interact more favorably or stronger than other colors, such as red, with a hydrogen peroxide based dentifrice.

In modified embodiments, part or all of a distal end of the handle can comprise a light-emitting compound such as an electrochemiluminescent material or other glow-in-the-dark type material, which may be implanted into the handle in various locations and formations or which may be integrally formed with part or all of a material of the handle. Additionally, or alternatively, part (e.g., a distal end) or all of the handle may be formed of a transparent material.

The treatment energy (e.g., electromagnetic radiation) may or may not be combined with a dentifrice, such as a paste, gel, cream, or powder, and may facilitate oral treatments including one or more of, for example, cleaning or reducing bacteria on or in hard or soft tissue, promoting blood circulation or healing of tissue, inhibiting caries, whitening teeth, preventing tooth demineralization, etching tooth enamel or dentin, and other similar methods.

As used herein, electromagnetic radiation or electromagnetic energy refers to monochromatic or polychromatic radiation or energy. In a preferred embodiment, electromagnetic radiation refers to light radiation or light energy. The treatment energy (e.g., electromagnetic radiation) can be delivered, for example, in treatment doses to, for example, increase a therapeutic or other effect on the tissue. In one example, a reaction rate of photosensitive agents, such as teeth whitening agents, can be enhanced. In accordance with one aspect of the present invention, the electromagnetic radiation may be substantially free from ultraviolet (UV) radiation. In addition, the wavelengths of the electromagnetic radiation may be provided between approximately 300 and 990 nanometers, or up to about 1 micron. Suitable means that may be used to generate the electromagnetic radiation, in addition to those mentioned, may include, for example, a semiconductor laser that generates monochromatic electromagnetic radiation or a LED that emits polychromatic, or alternatively, monochromatic, electromagnetic radiation. A non-limiting example of a laser source may comprise a Nd:YAG laser, although various other lasers having various wavelengths in the UV, visible and infrared (IR) spectrum, for example, may be implemented individually or in combinations.

The movement mechanism may be implemented with or without one or more wavelengths in various combinations (e.g., simultaneously or intermittently) of the treatment energy (e.g., electromagnetic radiation) and/or one or more dentifrices (e.g., multiple dentifrices at different but overlapping times), and may enhance or alter any of the actions or effects described herein and/or may provide other actions or effects to the tissue being treated. Actions or effects that may be imparted from one or more of the movement mechanism(s), the dentifrice(s) and the treatment energy or energies, can include, as a few examples, one or more of (a) cleaning or massaging of soft tissue such as the gingiva or tongue, (b) promotion of cleaning and bacteria reduction (e.g., removal of tarter, calculus or plaque; prevention of decay, periodontal and gingivitis treatment; and killing of germs,) or whitening of hard tissues, (c) surface agitation, (d) an enhanced reactive effect (e.g., enhanced oxidation of a peroxide cleaning agent on teeth), (e) biostimulation (e.g., photodynamic therapy or biotherapy) which may enhance circulation or other properties of tissue (e.g., aphthous ulcers or herpetic lesions) and which may promote one or more of healing, pain reduction, reduced sensitivity, bleeding gums, and inflammation, (f) rendering of tissue more receptive to other treatments (such as may occur with low level light therapy (LLLP)), (g) enhancement of efficacy (e.g., absorption) or receptiveness of tissues to topographical additives (e.g., bactericidal fluids such as those containing one or more of anesthetics, bactericidals, anti-viral components, and other medicines), (h) enhancement of halitosis detection (e.g., greater air circulation which may aid in speed or precision of halitosis detection or treatment) or treatment (e.g., augmented cleaning effects).

The device of the invention may also be provided with a circuit, and/or microprocessor (e.g., computer chip), for controlling, for example, one or more of any characteristic or functionality of the treatment energy source (e.g., electromagnetic radiation source) and/or the movement mechanism in accordance with, for example, desired or predetermined procedural steps or patient protocols or needs. Moreover, the circuit may be configured to control, for example, one or more of any characteristic of an electronic input/output device and a detector, either or both of which may be used in combination with (e.g., coupled to) the handle.

In addition to being configured to control, for example, one or more of any characteristic or functionality of the treatment energy source (e.g., electromagnetic radiation source), movement mechanism, electronic input/output device, and/or detector(s), the circuit and/or microprocessor may be programmable to further effectuate or optimize treatment protocols. For example, in a context of tooth-whitening, the programmable microprocessor may control parameters such as light, wavelength, brightness, power, or duration of emission, wherein such parameters may be programmed as presets, or may be operated manually by the user. The user may control the speed of whitening by selecting the wavelength, the brightness, the power, and the time of exposure. For in-office procedures, a clinician may decide the specific parameters suited for the patient. For out of office procedures, such as home use, the user may select one of the preset programs. As a particular example, a program may provide a higher light intensity for a relatively short duration. In addition, the oral device may include a sensor device that, through software control, informs the user when the process is completed or the treatment time has expired.

The electronic input/output device may comprise, for example, one or more of an audio playback and/or recording system and a video playback and/or recording system. In certain implementations, the detector may comprise one or more of an impedance, current, or microvoltage detector, a magnetic detector, a sonar (e.g., using vibration, ultrasound or other acoustic means) detector, an optical (e.g., using light scattering) detector, a visualization device (e.g., a single frame or video camera), and a gas detector. The detector can be used for detecting tissue conditions, such as, for example, in the case of oral applications, dental carries, periodontal disease, bronchitis, tumors, or halitosis.

According to an aspect of the present invention, a detector may be used in combination with the handle to detect conditions of tissues contacted by or disposed in a vicinity (e.g., a relatively close proximity) of the handle. The detector may or may not be operatively coupled to (e.g., in physical or data communication with) the handle. In exemplary embodiments, the detector may be coupled to or disposed on the electromagnetic radiation source (e.g., at or near an output end of a laser). In accordance with certain implementations, the detector may be disposed within or on an exposed surface of the handle. In exemplary embodiments, the detector may be molded within the handle. For instance, a detector for discerning at least one condition of a tissue (e.g., tooth or gingiva), by for example detecting one or more of a resistance/current/microvoltage, magnetic, sonic, and optical response of the tissue, may be embedded within the handle. In certain embodiments, the detector may be operatively coupled to the handle but disposed neither within nor on a surface of the handle. For example, the detector may employ one or more of visualization (e.g., an integral or stand-alone video camera), impedance, current or potential, magnetism, sonar and optical implementations to facilitate detection, discernment or collection of information (e.g., visual information in the case of a camera) regarding tissue conditions or tissue locations, such as, for example, plaque, calculus (tartar) or carries on a target (e.g., user's teeth or gingival).

In exemplary embodiments, a visualization device (e.g., camera) may be coupled (e.g., secured) to, near, or within a textured surface of a handle or may be coupled to or within another part of the handle, alone or in combination with, for example, an output tip of a treatment energy source (e.g., a laser source), which provides treatment energy. In other embodiments, a visualization device may be directly coupled (e.g., secured) to an output tip of a treatment energy source (e.g., a laser source) that provides treatment energy. For any of the embodiments described herein, the visualization device (e.g., camera) may comprise a visualization fiber optic leading to a remotely disposed camera, which is not on or near a textured surface of the handle or not otherwise on the handle or output tip. The visualization fiber optic may be disposed on or in a cannula (e.g., a cannula coupled to the handle), or, for example, otherwise disposed on or in the handle, and the handle further may contain one or more of the following, each of which may be disposed inside or apart from the cannula: a treatment-energy waveguide or output tip, a visualization light source, a fluid output, and an aspiration source (e.g., a calibrated aspiration source).

Fluids, such as liquids or air, can be directed over a lens of the camera and/or across a field of view of the camera to, for example, create a better viewing area, and/or aspiration can be applied for removing fluids from a vicinity of the lens or field of view. In addition to or as an alternative to the discussed fluid and aspiration techniques and structures for use in combination with, for example, a camera lens, water repelling coatings (e.g., Rain-X® Original Glass Treatment, made by SOPUS Products of Houston, Tex.) can be applied to the lens for enhanced visual clarity. According to one embodiment, washing part or all of the handle (e.g., toothbrush) with water can operate to clean the coated, or non-coated, camera lens. For embodiments wherein the handle comprises, for example, a toothbrush, modified embodiments may comprise dentifrices formed as, for example, non-foaming toothpastes or clear-gel toothpastes.

According to alternative embodiments, the detector may comprise a gas detector, implemented alone or in combination with any of the preceding detectors, structures and implementations, and configured to facilitate detection, discernment or collection of airborne-agent information (e.g., by sampling air near a target tissue for the presence of predetermined items or chemicals as known in the art) regarding tissue conditions or tissue locations, such as, for example, halitosis on a user's teeth, after which, for example, a handle may be loaded with a dentifrice (e.g., comprising an antiseptic or cleaning agent) in a manor similar to that previously discussed in order to address the condition.

Architectures and signal processing protocols for implementing impedance, current, potential, magnetic, sonic, optical, and airborne-agent data and signals to discern properties (e.g., the presence of treatable conditions) of targets (e.g., tissues) are known to those skilled in the art and are incorporated herein by reference. In one embodiment, the visualization device can comprise an intraoral video camera such as that manufactured by RFSYSTEMlab of Nagano, Japan and described at www.rfsystemlab.com. The intraoral video camera may be constructed with one or more light sources having wavelengths and associated circuitry designed to elucidate (e.g., visually differentiate) one or more tissue conditions. One system which may have relevance in this field of endeavor may comprise a DetecTar system, which is constructed for detecting subgingival calculus and which can be obtained from Ultradent Products, Inc. at www.ultradent-.com. Light sources having one or a plurality of wavelengths, when directed on tissue within an oral cavity alone or in combination with a coloring agent applied to the tissue, may operate to facilitate an identification of a tissue condition, such as caries.

In connection with (e.g., following a detection of) a treatable condition (e.g., a presence of plaque, calculus or carries) on or in a vicinity of a target (e.g., tissue), a treatment implementation may be configured (e.g., equipped, activated or programmed) on, within, or in connection/communication with the handle, or apart from the handle. The treatment implementation may comprise, for example, an implementation for application to the target and may comprise one or more of: an activated textured surface; a chemical (e.g., an organic enzyme); fluid (e.g., a water-jet operable via a button disposed on the handle); acoustics such as ultrasound (cf., a cavitron dental scaler) that according to the present invention may be used following suitable adjustments for frequency or ranges of movement to match intended functionalities such as cutting; a piezoelectric scaler (cf., a Satelec piezo scaler) that according to the present invention may be used, upon suitable adjustments for frequency or ranges of movement to match intended functionalities besides, for example, scraping, for one or more of etching in general, cavity preparation, shaping and etching dentin and enamel; air-abrasion; any mechanical cleaning or removing tool; and laser energy.

The mechanical cleaning or removing tool may comprise, for example, one or more of a blade, pick, scrapper, tongue scrapper disposed on a back of a brushing head opposite the bristles, etc.) A mechanical cleaning or removing tool may comprise, for example, a hand scaler in the form of a pick and/or blade that may be formed of or include, for example, a plastic or composite material having a rigidity sufficient to facilitate removal of tooth films or undesired materials, wherein the hand scaler can be formed in whole or in part into, for example, an elongated, pointed protrusion with one or more blade-like edges. Other embodiments may comprise harder materials or even metals for professional or more advanced models or implementations (e.g., removing stubborn calculus).

Any such tool, or other component described herein, may be sterilized using conventional means, such as UV light. In an embodiment wherein the treatment comprises UV light emitted through bristles of at toothbrush, a sterilization mode may be activated to cause the devise to sterilize the bristles with the UV light. For instance, in the case of a treatment condition comprising a presence of plaque on a tooth, the treatment implementation may comprise an isolating and/or vibrating textured (e.g., bristled) surface, a chemical plaque remover within a dentifrice and/or a plaque-remover implementation utilizing one or more of fluid, acoustics (e.g., ultrasound), air-abrasion, mechanical means and laser energy. In typical embodiments, an implementation (e.g., removing tool or laser) can be combined with (e.g., attached, formed together, etc.) a visualization device (e.g., a single frame or video camera) coupled to a handle (e.g., a toothbrush or wand) so that a user can, for example, identify treatment conditions (e.g., areas of plaque) and, in real time, use the implementation to treat the condition (e.g., remove the plaque) wherein feedback (e.g., immediate feedback) can provide verification of the efficacy of the user's removal efforts (e.g., on a user input/output device comprising, for example, a display combined with a makeup mirror, the display being configured, for example, to output a video feed from the camera).

In modified embodiments, a handle (e.g., a toothbrush) may be configured to emit fluid (e.g., as a mist, drops, sprays, a stream, etc.), which may comprise liquid and/or gas therefrom (e.g., from a head of a toothbrush or from an area near a cleaning surface), wherein the liquid or gas is stored in the head or body of the handle or fed remotely from a fluid line. The fluid (e.g., liquid such as an antibacterial and/or antiviral fluid/gel, Listerine, and/or gas) may additionally or alternatively be conditioned (e.g., flavored) and comprise or be combined, in whole or in part and in any combination with the ingredients described herein and/or any of the ingredients as described in U.S. Pat. No. 6,350,123, entitled FLUID CONDITIONING SYSTEM, the contents of which are incorporated herein by reference.

The treatment implementation may be configured, in whole or in part, at a time of manufacture or assembly of the handle, or otherwise before detection of the treatable condition, and/or at a time after detection of the treatable condition. Moreover, the configuring may be based upon one or more predetermined criteria and/or based upon information corresponding to the detection of the treatable condition. Furthermore, the treatment implementation may be configured to be applied relatively evenly over the target, or may be configured to be applied in such a manor as to provide greater concentrations of treatment (e.g., plaque-removal action) in certain locations such as, for example, locations detected (e.g., visually observed) or otherwise discerned or determined to contain the treatable condition. In other embodiments, the treatment implementation may comprise one or more of (a) any of preceding treatment implementations, and (b) one or more of a textured surface (which may or may not be part of a handle and which can be activated), chemical, fluid, acoustic (e.g., ultrasound), air-abrasion, and laser energy that can be applied, in whole or in part, to the target using (at least in part) structures or methods other than the handle, such as via a hand of a user. Thus, the treatment implementation may be applied to the target using one or more of a handle and an implementation other than the handle such as by way of a hand of a user.

According to exemplary embodiments, a detector (e.g., an optical detector) of the handle may discern a tissue condition (e.g., a cut on a user's tongue), after which a treatment (e.g., LLLT) may be directed onto the tissue as previously described. The treatment may be preceded by one or more of (a) a prompt by the electronic input/output device (e.g., via a speaker and/or display disposed on a handle charging and/or disinfecting station, the handle, a handle component (e.g., an electronic input/output device in communication with the handle), or a stand-alone component (e.g., a visualization device separate from the handle) and (b) a confirmation input by the user. Alternatively, the treatment may be initiated (e.g., automatically) without any prompt and/or user input.

In other embodiments, following detection, discernment or collection of information regarding conditions or locations of a tissue area of interest, iterative processes may be used to treat the tissue area of interest. For instance, in an embodiment wherein the handle comprises a toothbrush the input/output device may measure, record, and monitor shades of a user's teeth, wherein shade changes may be communicated to the user in any time or information format and/or downloaded or tracked on the input/output device or other processing device that can be coupled to, for example, the input/output device. For example, location information of a tissue condition may be collected and communicated to the user via the input/output device, followed by the performance of treatments as discussed above, followed by one or more repetitions of the preceding collection, communication, and treatment steps. In certain embodiments, following detection, discernment or collection of information regarding conditions or locations of a tissue area of interest, iterative processes may be used to facilitate further detection, discernment or collection of information regarding the conditions or locations of the tissue area of interest. For example, in a simple implementation, a speaker as described above may issue an audible indication (e.g., beep) when a detector is passed over an area likely to contain a treatable condition, thereby signaling such information to the user and/or signaling to the user that additional detection of the area may be warranted. According to an instance wherein the detector implements one or more of impedance, current, potential, magnetic, acoustic (e.g., sonic), light, visual and gas detection and comprises a wand movable by a hand of a user over oral tissue surfaces, the audible indication may signal to the user that additional detection of the area may be warranted in which case the user may move the wand back to a vicinity where the wand was positioned when the audible indication was issued. In certain embodiments, another audible indication may be issued when the wand is positioned back over the area and/or to signal, once again, to the user that additional detection of the area may be warranted in which case the user may again move the wand back over a vicinity where the wand was positioned when the most recent audible indication was issued.

According to one aspect of the present invention, the electronic input/output device can be configured to provide an indication (e.g., an audible or visual text message or an alarm) that a treatable condition should be brought to the attention of a professional (e.g., a dentist), such as in the case of detection of an advanced carries, periodontal disease, halitosis, or tumorous condition. For example, a scale of threshold levels may be programmed into the electronic input/output device for providing guidance (e.g., via audible or visual tones and/or worded messages) to the user on whether a detected treatable condition may or should be treated by the user at home and/or whether the condition should be brought to the attention of a professional.

According to other implementations, the electronic input/output device may comprise additional functionality and a user interface (e.g., one or more of a speaker, display and keys) for accessing such functionality, disposed on one or more of a handle charging and/or disinfecting station, the handle, a handle component (e.g., an electronic input/output device in communication with the handle), or a stand-alone component (e.g., an electronic input/output device separate from the handle).

In embodiments utilizing a display (e.g., as part of a handle charging and/or disinfecting station), the display may be part of or further comprise (e.g., be interchangeable with) a makeup mirror. For example, a 2-sided rotatable panel may comprise a makeup mirror on a first side and the display on a second side. In embodiments utilizing a speaker and/or a display (e.g., as part of a handle charging and/or disinfecting station), the display may further or alternatively comprise a telephone and/or videophone functionality.

Other embodiments utilizing a speaker and/or a display (e.g., as part of a handle charging and/or disinfecting station) may be programmed to indicate user information such as a prerecorded voice segment or photo of a user. In embodiments comprising multiple implements (e.g., attachments such as brushing heads), the speaker and/or a display may be programmed to indicate a unique prerecorded voice segment, text message, or photo (e.g., captured with a visualization device) of the user who owns the implement currently removed from the device (e.g., handle charging and/or disinfecting station). Thus, the voice segment, text message, or photo generated by the speaker or display upon removal by a user of his or her implement can provide a verification that the removed implement does indeed belong to the user.

The additional functionality may comprise an ability to play audio and/or visual information, such as vocabulary or foreign language lessons, music, news, or other prerecorded or real-time content.

In certain embodiments, content may be recorded into the electronic input/output device by the user (e.g., in the form of a memo recorded by the user the preceding evening), and in other implementations playback of the content may be performed according to a duration set by a user-defined timer. For example, in one instance language lessons may be played by the device for a predetermined or user-selected period (e.g., 2 minutes) with each use of the device, whereby the user may endeavor to perform an oral procedure (e.g., brushing or flossing) for the playback period (e.g., 2 minutes). In other instances a prerecorded message or messages (or other communication or signal) may remind the user at a preset time or times each day to perform an oral procedure, or the input/output device may comprise a motion detector and perform a reminder function (e.g., play a recorded message "Time to Brush."), for example, each morning upon the user first entering a predetermined space (e.g., a washroom) of the input/output device.

The electronic input/output device may be configured to interface (e.g., via wireless, USB, RJ11, RJ45, and other ports) with other computer components, such as personal digital assistants (PDAs), personal computers, handheld and other portable media playback devices, using communication protocols known to those skilled in the art, such as Internet, Ethernet, BlueTooth®, etc. Data concerning any of the above-discussed processes thus may by electronically transferred (e.g., via email) to and from the electronic input/output device. For instance, upon a determination that a treatable condition should be brought to the attention of a professional (e.g., a dentist), such as in the case of detection of an advanced carries or halitosis condition, the electronic input/output device can either automatically or under user control forward relevant information to the professional.

Referring more particularly to the illustrated embodiments, FIG. 1 depicts a handle coupled with an activated textured surface that can be implemented using one or more of, for example, a repetitive movement mechanism and a treatment energy source (e.g., electromagnetic radiation source). The handle and activated textured surface are embodied, as presently illustrated, in the form of an electromagnetic radiation emitting toothbrush 1 suitable for use with a container 31 of brushing compound; and the collection of implements can be disposed within a package 32. Other implementations of the illustrated embodiment, such as the embodiments depicted in FIGS. 2-6 which embodiments can apply equally to the disclosure set forth herein to the extent compatible or not mutually exclusive or to the extent modifiable by one skilled in the art to be compatible or not mutually exclusive, can have differing constructions of one or more of the handle and activated textured surface (e.g., electromagnetic radiation emitting toothbrush 1) and container 31 of brushing compound as will be apparent to those having skill in the art. The package 32 is shown schematically, and embodiments of the invention may use any suitable package design and configuration.

The general structure of the exemplary toothbrush 1 can be as disclosed in U.S. Pat. No. 5,306,143 entitled DENTAL HYGIENE APPLIANCE to Levy, the contents of which are incorporated herein by reference. Modified embodiments of the handle and activated textured surface may use, for example, other suitable electromagnetic radiation emitting toothbrushes or components.

The basic components of the toothbrush 1 include a handle 4 and an activated textured surface in the form of a brushing head 5. The brushing head 5 is constituted by a body 6 having a base surface 7 from which a set of tooth brushing bristles 8 project. The composition and form of the bristles 8, and the manner in which the bristles 8 are secured to the body 6, can conform to conventional practice in the toothbrush art. The ends 9 of the bristles 8 can comprise a cleaning surface that is used for scouring teeth and alike. Other embodiments may have other types of cleaning surfaces, such as, for example, a sponge or other type of foam.

The toothbrush 1 is further provided with means for directing radiation (e.g., monochromatic radiation) of a selected type from the body 6 in the direction of an arrow 10, which is generally parallel to the direction in which the bristles 8 project from the body 6. The radiation is emitted generally via the base surface 7 of the body 6. In modified embodiments of the invention, the radiation may be emitted from the handle 4, guided by the bristles 8, or any other suitable means for directing radiation to the ends 9 of the bristles, which form the cleaning surface of the illustrated embodiment.

The handle 4 is provided with an electromagnetic radiation source, which is embodied as a light-emitting device 14 for generating the electromagnetic radiation. Embodiments of the invention may use any suitable means for generating the electromagnetic radiation, such a semiconductor laser that generates monochromatic electromagnetic radiation or an LED that emits monochromatic or polychromatic electromagnetic radiation. The electromagnetic radiation source may comprise, according to certain examples, a plurality of LEDs, which may be perimetrically disposed along a surface of the handle, provided as a strip or array of LEDs, and/or embedded, molded, mounted, potted, or otherwise bonded on or within the handle. The LEDs may include side-mounted LEDs, surface-mounted LEDs, or a combination of surface- and side-mounted LEDs. An example of one suitable LED is the publicly available 1005 Series of LEDs from Marktech Optoelectronics (Latham, N.Y., USA). Examples of other electromagnetic radiation sources include, but are not limited to, one or more of heat emitting elements, LEDs, lasers or laser diodes, arc lamps, incandescent lamps, halogen lamps, neon lamps, and fluorescent sources. The electromagnetic radiation sources may emit electromagnetic radiation from, for example, ultraviolet to visible to infra-red light. In one embodiment, infra-red spectral energy may be implemented. The light sources may be provided at predetermined distances, for example, one LED per tooth, or may be provided relatively close together. The particular spacings of LEDs can be determined and chosen to optimize desired treatments (e.g., whitening or cleaning) to be provided by the handle and/or activated textured surface alone or in combination with one or more of a repetitive movement mechanism and an electromagnetic radiation source.

When surface-mounted LEDs are utilized, according to certain embodiments, contacts can be provided on the surface of a light source panel. Generally, in accordance with certain combinations utilizing certain constructions of surface-mounted LEDs and/or any other electromagnetic radiation source, a light source panel can comprise one or more layers of electromagnetic sources (e.g., optical fibers or fiber optic pipes). The optical fibers may be woven together. Multiple layers may provide more efficient use of the energy from the electromagnetic radiation source, and may enhance the brightness and uniformity of the light emitted from the light source panel to the target tissue area (e.g., the dentifrice and teeth). The panel of woven optical fibers may be molded or embedded in the handle. In another example, light may be emitted from a single side of the panel with a relatively high intensity, and a reflective panel may be provided attached to the outer layer of woven optical fibers. According to modified embodiments, a diffuser panel may be provided to increase the uniformity of the light on the tooth surface. One example of a suitable optical fiber panel is the Lumitex® panel (Lumitex, Inc. Strongsville, Ohio, USA), as disclosed in U.S. Pat. No. 5,613,751, entitled LIGHT EMITTING PANEL ASSEMBLIES, the contents of which are hereby incorporated by reference.

The electromagnetic radiation source may additionally or alternatively comprise an organic or polymeric thin-film of luminescent material. Examples of potential compounds or agents used in organic or polymeric thin-film luminescence include, but are not limited to, end-capped oligothiophenes, tris-chelated polypyridyl ruthenium (II) complexes, polyphenylenes, doped tris-8-(hydroxyquinoline)aluminum, indium tin oxides, polyfluorenes, vinylene-bridged triphenylamine dimers, rhodamine 6G, bicarbazyles, 1,1,4,4-tetraphenyl-1, 3-butadiene-doped polymeric Langmuir-Blodgett films, inorganic CdSe nanocrystals, carbazole-substituted polyacetylenes.

The brushing head 5 is shown having a lens 18, one or more semitransparent mirrors 20 and a fully reflecting mirror 22. In the illustrated embodiment of the invention, the electromagnetic radiation produced by light-emitting device 14 is in the form of a small diameter collimated beam extended along an axis corresponding to the longitudinal axis of the handle 4 and the head 5. The mirrors 20 and 22 are oriented at an angle of 45° to the beam axis, and the lens 18 is constructed and arranged to give the electromagnetic radiation beam a slightly diverging form such that the beam will diverge to an area essentially coextensive with the area occupied by the mirror 22. Modified embodiments of the invention, such as disclosed with reference to FIGS. 5 and 6, may use other arrangements for directing the electromagnetic radiation generating means to the cleaning surface of the brushing head 5.

The body 6 may itself be made of a plastic which is transparent to the electromagnetic radiation so that portions of the radiation are reflected in the direction 10 by the mirrors 20, and the remaining radiation is reflected by the mirror 22. The optical system constituted by the lens 18 and the mirrors 20, 22 is arranged to cause radiation to traverse an area, which is at least approximately coextensive with the area covered by the ends 9 of the bristles 8. However, the radiation area may, depending on the particular operations to be performed, extend over a smaller or larger cleaning surface. Modified embodiments of the invention may use other optical system arrangements.

A modified embodiment is illustrated in FIGS. 2-4. The mirrors 20, 22 are replaced with reflective surfaces. The reflective surfaces can be formed on the interior surfaces of the outer, stepped portion of the head of the toothbrush. The reflective surfaces may comprise foil or foils, for example, which are embedded into the plastic and wrapped, for example, around the back and sides of the stepped portion of the head. Other materials and/or types of reflective surfaces may be used to increase, decrease, and/or change a distribution of radiation transmitted through the bristles.

In the exemplary embodiment of FIG. 2, the head tapers from a diameter of 0.440 units, to a diameter of 0.287 units just before the stepped portion. This diameter, which is just before the stepped portion, can be increased to facilitate greater transmission of radiation to the stepped portion or, in other embodiments, can be decreased to attenuate an amount of radiation transmitted to the stepped portion. A width of the head, which is 0.430 units as shown in FIG. 4, may similarly be increased to facilitate greater transmission of radiation through the bristles or, in other embodiments, may be decreased to attenuate an amount of radiation transmitted through the bristles. The number, angles, sizes, etc. of the steps forming the reflective surfaces may be changed to increase, decrease, and/or change a distribution of radiation through the bristles.

In other embodiments of the invention prior-art toothbrushes equipped with a light source, which illuminates the brushing region and which provides beneficial radiation to the tooth surface, can be used. Examples of illuminating toothbrushes are disclosed in U.S. Pat. No. 5,306,143 entitled DENTAL HYGIENE APPLIANCE; U.S. Pat. No. 5,160,194 entitled TOOTHBRUSH WITH EXTERNALLY ILLUMINATED BRISTLES; U.S. Pat. No. 5,030,090 entitled OPTICAL TOOTHBRUSH AND METHOD OF USE; and U.S. Pat. No. 4,779,173 entitled ILLUMINATED BRUSH DEVICE, all of which are expressed incorporated herein by reference in their entireties.

The handle 4 can include a power cord 30 (FIG. 1) which may be plugged into a wall outlet in order to supply operating power to the light-emitting device or devices 14. Other embodiments of the invention may have a replaceable or rechargeable battery in the handle 4 as the power source for the light-emitting device(s) 14.

A modified embodiment is illustrated in FIGS. 5 and 6, in which like parts are labeled with like reference numbers preceded by "5"s and "6"s and wherein the preceding disclosure is incorporated here to the extent compatible or not mutually exclusive or to the extent modifiable by one skilled in the art to be compatible or not mutually exclusive. The figures depict a toothbrush 1 having a handle 4 coupled with an activated textured surface in the form of a brushing head 5 that can be implemented using one or more of, for example, a repetitive movement mechanism and a treatment energy source (e.g., electromagnetic radiation source).

The ends 9 of the bristles 8 can comprise a cleaning surface that is used for scouring teeth and the like. The toothbrush 1 is further provided with one or more radiation sources. In the illustrated embodiment, the radiation sources comprise a plurality of LEDs that direct electromagnetic radiation of a selected type from the body 6 in the direction of an arrow 10, which can be, for example, generally parallel to the direction in which the bristles 8 project from the body 6. In other embodiments, electromagnetic energy (e.g., light) may be emitted from the handle (e.g., brushing head) at different light angle configurations. One implementation comprises the brushing head emitting electromagnetic energy along a line of propagation that forms an angle less than about 90 degrees relative to the cleaning surface and/or that forms an angle greater than 0 degrees relative to the direction of the arrow 10. A particular implementation may comprise, for example, the brushing head emitting electromagnetic energy along a line of propagation that forms an angle of about 45 degrees relative to the cleaning surface and/or that forms the same angle relative to the direction of the arrow 10. In other embodiments, other particular angles between 0 and 90 degrees may be used. In one embodiment, the electromagnetic energy can be emitted through the bristles themselves and/or part or all of the bristles may be angled between 0 and 90 degrees to effectuate the above discussed angles of propagation of electromagnetic energy, and/or in another embodiment electromagnetic energy can be emitted from a backside of the brushing head.

In certain implementations, the electromagnetic radiation source can comprise one or more light sources and can be disposed on the handle (e.g., an end of the handle opposite the bristles) or routed to the handle via, for example, a fiber optic. In typical embodiments, the treatment energy source can comprise a light source that is configured to emit one or more of coherent or non-coherent light at a single or multiple wavelengths (e.g., at the same or different times), and can comprise one or more of a light emitting diode (LED), an optical fiber panel, an electrochemiluminescent material, a flashlamp, an optical fiber bundle, and combinations thereof. The one or more treatment energy sources (e.g., electromagnetic radiation sources such as LEDs) can be disposed anywhere from a proximal end of the handle 4 to a distal end of the handle 4 near the set of tooth-brushing bristles 8, and can be coupled to output treatment energy from or through one or more of (a) portions of a base surface 7 on the brushing head 5 that are not covered by projecting bristles 8, (b) interior portions of bristles 8 extending from the base surface 7 of the brushing head 5 wherein the bristles 8 function at least in part as treatment energy guides, and (c) a surface of the brushing head 5 opposite the base surface 7. Each treatment energy source (e.g., electromagnetic radiation source) may be coupled to a plurality of treatment energy guides (e.g., fiber optics) for directing treatment energy to and/or outputting treatment energy from one or more of (a), (b) and (c). An example of an embodiment having a plurality of treatment energy sources and treatment energy guides can comprise 5 LEDs, disposed in or near a proximal end of the toothbrush 1, that feed into 5 corresponding rows of output waveguides, which terminate at and output light from the base surface 7, wherein each row of output waveguides comprises a plurality of output waveguides.

As touched on above, the treatment energy (e.g., light) source(s) can be configured to emit one or more of coherent or non-coherent treatment energy at a single or multiple wavelengths and/or wavelength bands, at the same or different (e.g., multiplexed) times, and can comprise, for example, one or more of an LED, an optical fiber panel, an electrochemiluminescent material, a flashlamp, an optical fiber bundle, and combinations thereof. The number of light sources can be selected depending on, for example, wavelength (e.g., wavelength as a determinant of absorption strength of target) and power to be used. Thus, for example, a plurality of the same or different light sources can be activated simultaneously or time-multiplexed.

In embodiments wherein multiple layers (e.g., coatings of different materials) or substances are embedded on, within, between, or in other vicinities of the bristles, alone or in combination with any of the preceding items being disposed, for example, on the base surface 7 (e.g., of a brushhead cartridge), mounting structure 7" and/or in a dentifrice (e.g., paste), different combinations of layers, which are specific to different interactions between the treatment energy (e.g., light) emitted by the toothbrush, can be selected to produce specific effects. The multiple layers may be engineered to release (e.g., be dissolved and/or activated at least in part) at different times, which differing times may correspond in whole or in part to one or more of the different times of treatment energy emissions. Individual layers can provide one or more benefits, such as, for example, better hygiene, reduced plaque, treatment of gingivitis, bacteria destruction, tooth whitening, caries location, biotherapeutic benefits through biostimulation such as reduced bleeding of gums, reduced inflammation, reduced pain and sensitivity. With regard to bacteria destruction, treatment energies may be engineered (e.g., electromagnetic radiation, such as UV light, selected to have suitable wavelength and power density characteristics) to directly interact with and destroy bacteria, alone or in combination with treatment energies being configured to work in combination with one or more layers of dentifrice to destroy bacteria.

According to certain implementations, such as, for example, an embodiment corresponding to the brushhead of FIG. 11A, a toothbrush may output a first treatment energy in combination with a release of a first dentifrice (e.g., a first layer of dentifrice) from a brushing head and may output a second treatment energy in combination with a release of a second dentifrice (e.g., a second layer of dentifrice) from the brushing head. The first dentifrice may be the same as or may differ in at least one characteristic from the second dentifrice, and/or the first treatment energy may be the same as or may differ in at least one characteristic from the second treatment energy. Any one or more (e.g., up to all) of the first dentifrice, the first treatment energy, the second dentifrice and the second treatment energy may be emitted or released at the same or different times. For instance, a dual-wavelength toothbrush may comprise a first treatment energy source that is activated in combination with a release of a first layer of dentifrice from a brushing head and a second treatment energy source that is activated in combination with a release of a second layer of dentifrice from the brushing head.

In one example, a first dentifrice layer (i.e., a proximal layer closest to the base surface) can comprise a peroxide base, and a second dentifrice layer (i.e., a distal layer located distally of or further away from the base surface than the first layer) can comprise a photosensitizer having at least one property that is different than the peroxide base. The first layer can be activated by treatment energy sources that stimulate the peroxide or can facilitate activation of or by way of a photosensitizer, e.g., via or including an organic compound. According to certain embodiments, treatment energies can comprise laser outputs, ranging from about 250 nm (e.g., UV) to about 250 nm, that are engineered (e.g., as a result of their relatively short wavelengths) to penetrate through at least a part of the first layer (e.g., with minimal activation thereof) and be absorbed by or otherwise interact with at least a part of the second layer. Thus, a substantial portion of treatment energy, such as from a first laser, may penetrate through the first layer and be substantially absorbed by the second layer so that at least one ingredient (e.g., of the second layer) is directly and/or indirectly activated.

Subsequently, another output of treatment energy (e.g., the same as, or with one or more properties differing from, the initial treatment energy) can be provided by way of, for example, an internal timer or a user pressing a button. The other output treatment energy can be generated, for example, by a second laser and can be absorbed by or otherwise interact with at least a part of the first layer. The second treatment energy may comprise a wavelength having a deeper penetration than that of the earlier-generated treatment energy. For instance, the other treatment may comprise an IR or near-IR wavelength, and the first layer may comprise a photosensitizer such as a dark pigment that absorbs the IR or near-IR radiation. In an exemplary implementation, a substantial portion of the other laser energy may be substantially absorbed by the first layer so that at least one ingredient (e.g., of the first layer) is directly and/or indirectly activated.

The second layer may be activated by a first laser during a first period of time followed by the first layer being activated by a second laser within the toothbrush during a second period of time, or, as another example, both layers may be activated by one or more of a first laser and a second laser (e.g., disposed within the handle) at the same time. In any of the embodiments described herein, more than two layers, and/or more than two treatment energy sources and/or treatment energies may be provided. In one embodiment, one or more components in each of both the second layer and the second layer may be activated by a first laser at the same or different points in time, and/or one or more other components in one or more of the second layer and the first layer may be activated by a first laser and/or a second laser at the same or different points in time. Subsequently, one or more further components in one or more of the second layer, the first layer, and a third layer, may be activated by one or more of a first laser, a second laser, and a third laser at the same or different points in time. The second layer may be activated by a first laser during a first period of time followed by the first layer being activated by a second laser within the toothbrush during a second period of time, or, as another example, both layers may be activated by one or more of a first laser and a second laser (e.g., disposed within the handle) at the same time.

In another embodiment, a single layer of dentifrice comprising components of the first layer and the second layer can be activated by one or more laser sources at one or more points in time as discussed above. According to yet another embodiment, bristles operating as waveguides can be connected/coupled to each of a plurality of treatment energy sources, wherein, for example, bristles having shorter lengths are coupled to the first treatment energy source and bristles having longer lengths are coupled to the second treatment energy source. Other modifications can comprise treatment energy from the first treatment energy source being relatively defocused (e.g., using lenses) on the first layer and focused (e.g., using the same and/or different lenses or configurations) on the second layer so that the second layer receives a substantially greater power density of treatment energy from the first treatment energy source. In one implementation, one or more spot sizes projected on the second layer from the first treatment energy source are substantially greater than one or more spot sizes projected on the first layer from the first treatment energy source so that the second layer receives a substantially greater power density of treatment energy from the first treatment energy source. According to another implementation, the second layer can be one or more of a relatively viscous layer, a layer that is relatively less hydrated and a layer that has a greater density (e.g., is a solid), relative to the fist layer, so that one or more components (e.g., substantially all) of the second layer are released later in time than one or more components (e.g., substantially all) of the first layer. In other embodiments, one layer can comprise peroxide and another layer can comprise alcohol or an organic compound, so that mixing of the two layers can provide a desired effect such as discussed herein. The two layers may comprise separated components for enhanced shelf-life (e.g., peroxide in one layer and baking soda in another layer) and may be constructed to mix together at substantially the same time (e.g., layers mix immediately upon an initiation of brushing) or to mix at different pints in time.

In certain embodiments, wavelengths of light sources can be engineered to activate peroxide compounds within dentifrices, directly or indirectly, such wavelengths including, for example, about 254 nm, about 265 nm, about 280 nm, about 295 nm, about 310 nm, about 313 nm, about 340 nm, about 370 nm, and about 460 nm. Light sources may emit these exemplary wavelengths in relatively discrete forms or as bands of about 10 nm to about 15 nm, total, centered about the mentioned peaks. In modified embodiments, the bands may be up to about 50 nm in width, centered about the above-mentioned peaks.

Examples using, for instance, ultraviolet wavelengths, to indirectly activate peroxide in dentifrice solutions/compositions containing organic compounds such as solid, primary, or secondary alcohol, can comprise activating light sources to emit wavelengths of, for example, about 365 nm or about 313 nm, to thereby activate the peroxide. When hydrogen peroxide is diluted in an alcohol based composition, the alcohol can be destabilized by irradiation with, for example, impinging electromagnetic energy (e.g., light) having wavelengths of about 314 nm or about 365 nm, thereby activating the hydrogen peroxide (e.g., causing it to oxidize and emit oxygen bubbles and/or produce peroxy radicals (e.g., ROO—) or hydroxyl radicals (e.g., OH—)). In one implementation, hydrogen peroxide may be configured in a dentifrice to interact with alcohol in Listerine type solution. In modified embodiments, any of the proceeding wavelengths or subsequently described wavelengths can be implemented for direct or indirect activation of various components (e.g., peroxides) in compositions/solutions such as dentifrices.

In typical embodiments, a power per light source can range from about 0.1 mW to about 500 mW. According to a few particular implementations, an array of about 50 light sources in a brushing head can comprise individual light sources of about 1 mW each, an array of about 20 light sources in a brushing head can comprise individual light sources of about 20 mW each, an array of about 2 to 6 light sources in a brushing head can comprise individual light sources of about 100 mW each, and an array of only a single or a few light sources in a brushing head can comprise an individual light source or sources of about 500 mW each.

In the context of one or multiple light sources, and one or more layers of coatings, and in the context of selecting particular combinations of light sources and components in dentifrices to obtain desired or predicted results, exemplary wavelengths of light sources may of course vary depending on desired results and various particulars of engineered embodiments. Light sources can be selected, for example, to be between about 200 nm and about 400 nm (e.g., UV to visible range) to activate hydrogen peroxide in a dentifrice gel or paste or to activate a combination of hydrogen peroxide and an organic compound. Other light sources can be selected, for example, to be between about 400 nm and about 1500 nm (e.g., visible near infrared) to activate a dentifrice with a photosensitizer (e.g., photodynamic therapy (PDT) photosensitizers or other photosensitizers (e.g., dark color pigments or food/cosmetic coloring ingredients) matched with particular wavelengths for enhanced or desired or otherwise sought absorptions or effects), which photosensitizer can be used for example to destabilize the peroxide. According to other implementations, light sources can be selected to be between about 1500 nm to about 3500 nm (e.g., middle infrared and up) to activate, for example, hydrogen peroxide through direct absorption or indirect absorption by way of a photosensitizer (e.g., an OH based compound or water) wherein photosensitizers can be matched, for example, with particular wavelengths for desired effects, such as strong absorption, examples of which can include wavelengths of about 2779 nm or about 2771 nm for water, hydroxide or hydrogen peroxide.

In addition to providing a user with an option for choosing to replace brushing heads after relatively short periods of time for attenuating an accumulation of antigens or pathogens on the brushing cartridge, another feature of the present invention comprises providing a efficient and convenient cleaning and disinfecting system for the toothbrush, to thereby facilitate and encourage a safer and more sanitary operation of items of the toothbrush that are, for example, subjected to repetitive use but not disposable. For such non-disposable items, such as the handle, or the handle including the brushing head in embodiments wherein the brushing head is not disposable or not disposed on a frequent (e.g., daily) basis, a bath can be provided for cleaning all or part of the handle (e.g., a neck portion thereof) and/or brushing head (e.g., of sterilizing solution such as a Listerine® type solution that may be distributed via a nebulizer onto surfaces of the toothbrush in a storage chamber or that may be automatically dispensed from and/or into a disposable reservoir via a puncture to at least partially submerge a neck or distal end of the toothbrush in the solution during storage or charging). A modified embodiment may incorporate, in addition to or as an alternative to the bath, an acoustic (e.g., ultrasonic) decontamination or sterilization unit.

The brushing head 5 can be constituted by a body 6 having a base surface 7 from which a set of tooth brushing bristles 8 projects. The electromagnetic radiation source may comprise, according to certain examples, a plurality of LEDs, which may be provided as an array of mounted LEDs, wherein each LED can be removably secured to the handle 4 and fitted into (e.g., pushed through) a corresponding slot in the brushing head 5. As presently illustrated, each electromagnetic radiation source may comprise a waveguide disposed distally of the LED to direct electromagnetic radiation in a general direction of the arrow 10. The waveguides may comprise, for example, cylindrical or conical shapes having reflective internal surfaces as known in the art. In certain embodiments, implemented with or without the waveguides, the mounting structure may be formed of a transparent material to facilitate propagation of electromagnetic radiation therethrough and, for example, in a general direction of the arrow 10.

In addition, according to certain illustrated embodiments, brushing head 5 can be formed as an implement that is readily detachable from handle 4. This construction can allow for a plurality of brushing heads 5, each used by a different individual for example and/or each used over a different period of time, to be mounted on handle 4 for use. In certain embodiments, such as that illustrated in FIGS. 5 and 6, each brushing head 55 may be removable and disposable, and may be formed to fit into or onto, or to otherwise be coupled to, receiving structure of the handle 54. According to embodiments wherein the brushing head 55 is removable, the brushing head 55 may further comprise a mounting structure 7', which may be constructed, for example, to engage receiving structure of the handle 54. In representative embodiments, the mounting structure 7' is configured not to block substantially electromagnetic energy emitted from the electromagnetic radiation source propagating in the direction of arrow 60.

The mounting structure 7' may be disposed, for example, on the brushing head 55 opposite to the base surface 57 and may be constructed to engage receiving structure of the handle 54. According to other embodiments, in addition to or as an alternative to mounting structure 7', one or more mounting structures 7" may be disposed, for example, on a perimeter portion of the brushing head 55, and may be constructed to engage receiving structure of the handle 54. A mounting structure 7' may be disposed, for example, on a portion of the brushing head that is adjacent to the base surface 57.

Each brushing head may comprise, according to one aspect of the present invention, a substantially planar mounting structure, which is disposed opposite to a substantially planar base surface (e.g., opposite to the set of tooth brushing bristles according to embodiments wherein tooth brushing bristles are attached to base surface). In accordance with another aspect of the present invention, each brushing head may comprise a mounting structure and a base surface, wherein at least a portion of the base surface is not shared (e.g., does not overlap) with the mounting structure. The base surface can be disposed, in whole or in part, opposite to the mounting structure. In modified embodiments, the mounting structure can be juxtapositioned, in whole or in part, next to the base surface. As another embodiment, a perimeter surface may border at least a part of a juncture between the mounting structure and the base surface. In accordance with yet another aspect of the present invention, each brushing head may comprise a mounting structure, a base surface disposed opposite the mounting structure, and a substantially rectangular, or oval, perimeter surface bordering the mounting structure and the base surface. The oval perimeter may comprise, for example, a circular perimeter. Another aspect of the present invention can comprise each brushing head having one or more of a non-smooth and a non-planar mounting structure, and may further comprise receiving structure of the handle being constructed to receive and engage the mounting structure. Any of the preceding embodiments, and other embodiments disclosed herein, may be implemented alone or in combination with any of the other embodiments or aspects described herein, in any combination or permutation, to the extent compatible or not mutually exclusive or to the extent modifiable by one skilled in the art to be compatible or not mutually exclusive.

Another aspect of the present invention can include each brushing head having a maximum diameter, measured in a given direction transverse to the arrow 10, wherein the receiving structure also comprises a maximum diameter, measured in the given direction, that is about the same length as the maximum diameter of the brushing head.

The handle can comprise, according to another aspect of the present invention, a bay constructed to receive (e.g., surround, encompass or Contact) a part of each brushing head. The part of the brushing head can comprise, for example, at least one part or side of the brushing head. The at least one part or side may comprise, for example, two, three, four or five surfaces. In modified embodiments, the receiving structure can comprise a bay that is constructed to encompass at least about 20%, or in other embodiments at least about 30%, of a total surface area (excluding exposed surfaces of the bristles themselves) of the brushing head. In further embodiments, such as illustrated in FIGS. 5 and 6, the receiving structure comprises a bay that is constructed to receive (e.g., surround, encompass or contact) at least about 40% of a total surface area (excluding exposed surfaces of the bristles) of the brushing head 55.

For embodiments wherein the receiving structure comprises a bay configured to receive a portion of the brushing head, the receiving structure can have at least one feature with a shape that is complementary to a shape of a corresponding feature of the brushing head fitting into the bay.

A contacting portion of the mounting structure can be defined as a portion that contacts a corresponding part of the receiving structure. The part of the receiving structure contacted by the portion of the mounting structure can comprise a shape or feature that is complimentary to the portion of the mounting structure. According to another aspect of the present invention, a feature or topography of a portion of the mounting structure that contacts a corresponding part of the receiving structure can be complimentary to a feature or topography of the part of the receiving structure contacted by the mounting structure. The feature or topography of the portion of the mounting structure can comprise a protuberance, or an indentation or aperture, and the feature or topography of the part of the receiving structure contacted by the mounting structure can comprise an indentation or aperture, or a protuberance, respectively. In a typical implementation, a protuberance of a portion of the mounting structure can be constructed to be coupled (e.g., establish at least a partial contact) with an indentation or aperture of the receiving structure. The indentation or aperture can have a shape that is complementary to a shape of the protuberance. According to another embodiment, a feature or topography of the portion of the mounting structure comprises two or more of a protuberance and an indentation or aperture, and the feature or topography of the part of the receiving structure contacted by the mounting structure comprises two or more of a protuberance and an indentation or aperture.

Another feature of the present invention may comprise a brushing head having one or more of a non-smooth and a non-planar mounting structure, or comprising a mounting structure having one or more of a non-smooth and a non-planar portion. A handle may comprise one or more of a non-smooth and a non-planar receiving structure, or may comprise a receiving structure having one or more of a non-smooth and a non-planar portion. A receiving structure of the handle may be constructed to receive and engage, or to be received and engaged by, the mounting structure or the portion of the mounting structure. One or more non-smooth or non-planar mounting structures or portions of mounting structures may correspond to (e.g., receive, surround, encompass or contact) one or more non-smooth or non-planar receiving structures or portions of receiving structures of the handle and/or one or more non-smooth or non-planar receiving structures or portions of receiving structures of the handle may correspond to (e.g., receive, surround, encompass or contact) one or more non-smooth or non-planar mounting structures or portions of mounting structures. Any of the non-smooth or non-planar mounting structures or receiving surfaces, or portions thereof, may comprise features, such as, to name a few examples, one or more of latches, protuberances, indentations, apertures, and combinations thereof.

Further aspects of the present invention include brushing heads provided in the form of brushhead cartridges. Each brushhead cartridge may be constructed, in whole or in part, to resemble the brushing head 55 of FIGS. 5 and 6. In accordance with one aspect of the present invention, a toothpaste carriage system can be provided wherein a dentifrice (e.g., toothpaste) disposed within a reservoir of the carriage can be applied to bristles of a brushhead cartridge upon a user pressing against an internal surface of the carriage. In another aspect of the present invention, a dentifrice dispenser (e.g., stand-alone tube of toothpaste) can be provided with separate compartments containing at least in part separate ingredients wherein the separate ingredients are combined upon dispensing of the dentifrice (e.g., toothpaste) from the dentifrice dispenser.

Figure 7:
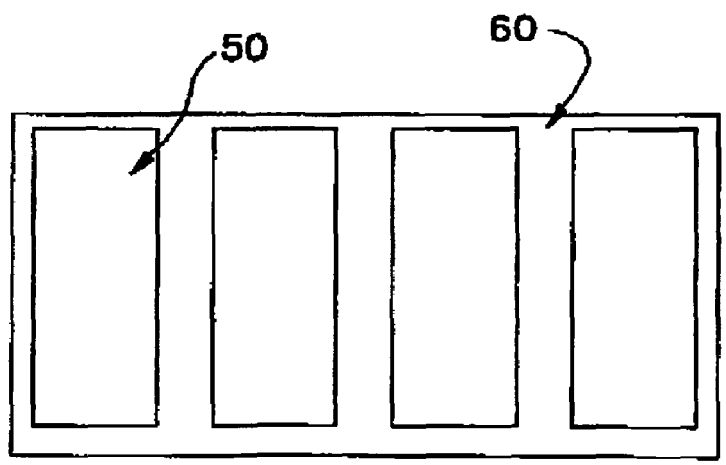
FIG. 7 depicts a plurality of brushhead cartridges stored in complimentarily-shaped bins of a carriage.

With reference to FIG. 7, a plurality of brushhead cartridges mare depicted wherein each brushhead cartridge 50 is stored in a complimentarily-shaped bin of a carriage 60. With the arrangement, a user can be provided with an ability to load new brushheads of the same type or of different types, incorporating, for example, various arrangements of dentifrice, paste or gel. For example, brushhead cartridges may be fabricated to comprise zinc impregnated fibers/bristles for therapeutic purposes such as treatment of colds and/or silver impregnated fibers/bristles for decontamination. Moreover, a user may choose to dispose of and replace each brushing head after a relatively short period of time (e.g., each brushing or each day) to thereby attenuate a buildup of or exposure to contaminants, such as antigens or pathogens, on the brushing cartridge. Other selections and combinations of brushhead cartridges, such as brushhead cartridges having various coatings (e.g., layers of coatings of different materials) or substances embedded on, within, between, or in other vicinities of the bristles, alone or in combination with any of the preceding items being disposed, for example, on the base surface 7, mounting structure 7" and/or in a dentifrice (e.g., paste) pre-applied to the brushhead cartridge, are contemplated, as well. Additionally, or alternatively, a user can be provided with an ability to load new brushheads having different functions, such as, for example, a cleaning function being provided by a cleaning surface (e.g., bristles) of a first brushhead cartridge and a plaque removing function being provided by an implement (e.g., a pointed, sharpened or other suitably-shaped implement) of a second brushhead cartridge. FIG. 7 and others which follow depict examples of such a second brushhead cartridge.

For storage, each of the brushhead cartridges can be constructed to latch, snap or otherwise fit into a corresponding (e.g., complementarily-shaped) bin of the carnage. Subsequently, prior to use, a brushhead cartridge can be removed from (e.g., unlatched or snaped-out of) one of the complementarily-shaped bins of the carriage and, in preparation for use, attached to (e.g., latched or snaped-into) a corresponding (e.g., complimentarily-shaped) bay or other receiving structure of the handle. Shapes and functions of the brushhead cartridges, correspondingly-shaped bins and carriages, and correspondingly-shaped bays or other receiving structures of the handle, can be, in whole or in part, with or without modification(s) that may be known or implemented by those skilled in the art, similar or identical to those of any known cartridge/carriage/handle combinations, such as any known razor blade cartridge/carriage/handle combination.

Additionally, with regard, for example, to the embodiment of FIG. 1, lens 18 may form a unit with handle 4, so that each of the brushing heads 5 need not be provided with its own lens. A similar construction may be implemented with the embodiment of FIGS. 5 and 6, wherein a lens (not shown) is provided at an output (e.g., distal) end of each LED and secured to the handle 4 so that replacement of a brushing head 5 does not require replacement of the lenses. Such configuration may reduce the costs associated with manufacturing each head 5. Modified embodiments of the invention may have the electromagnetic radiation supplied from a source external to the toothbrush 1 via, for example, a fiber-optic cable, as is known to those skilled in the art. Any of the preceding or following embodiments, and other disclosure herein, may be implemented alone or in combination with any of the other embodiments or aspects described herein, in any combination or permutation, to the extent compatible or not mutually exclusive or to the extent modifiable by one skilled in the art to be compatible or not mutually exclusive.

Referring to the FIGS. 7-14, each cartridge may comprise a shape having a hollow interior or concave region for accommodating a head of a toothbrush. In one implementation, each cartridge can comprise a six-sided rectangular shape with two of the sides open. In other words, four sides of the cartridge may comprise four walls and two sides of the cartridge may be open. The walls may comprise, for example, a base structure, two side walls, and an distal end wall. The two open sides may comprise a top side and a proximal side of the six-sided rectangular shape. The base structure can have bristles flush mounted and/or integrally formed into the base structure to extend away from an interior of the cartridge using manufacturing techniques known to those skilled in the art. For example, the bristles can be over-molded into the base structure of the cartridge. The bristles typically will be fabricated to extend radially outwardly from the base structure.

In an illustrated embodiment, the cartridge can comprise at least one transparent wall (e.g., the base structure for holding the bristles) wherein one to three of the remaining walls may be transparent or, optionally, opaque. The bristles may comprise transparent structures in one embodiment. In another embodiment, all four of the walls may be transparent. According to yet another embodiment, the cartridge may comprise a continuously-curved structure corresponding to the base wall and the two side walls forming a half-cylinder shape, a closed end (e.g., a distal end wall), and an open end (e.g., a proximal end wall).

Figure 8:
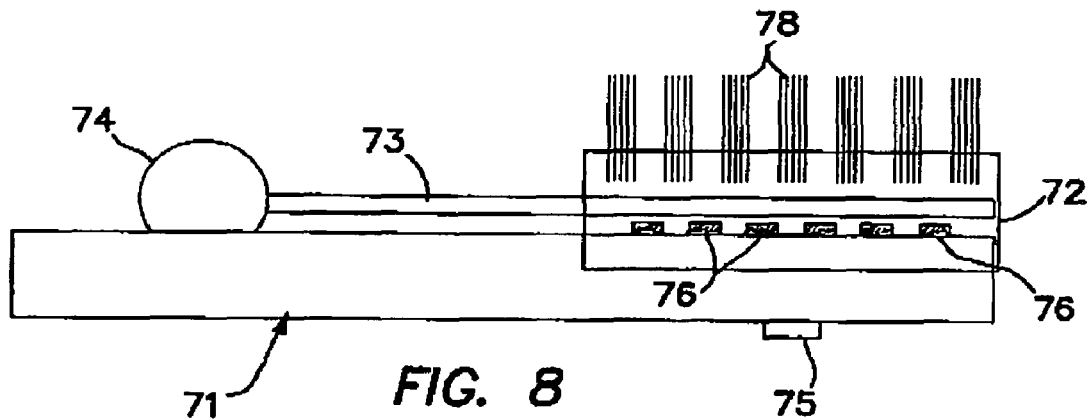
Figure 9:
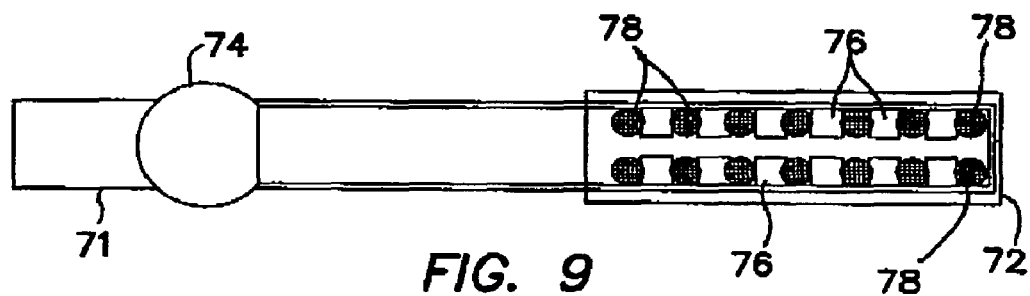
Figure 9A:
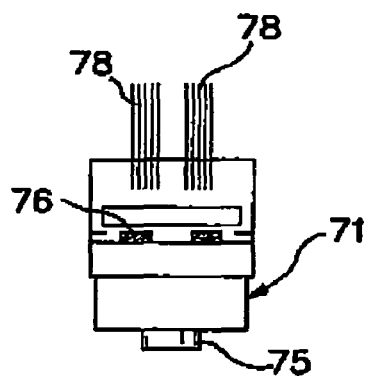
Figure 9B:
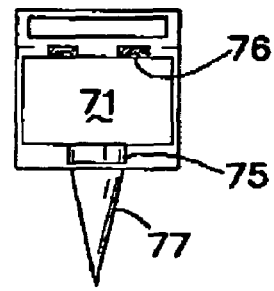
Figure 12A:
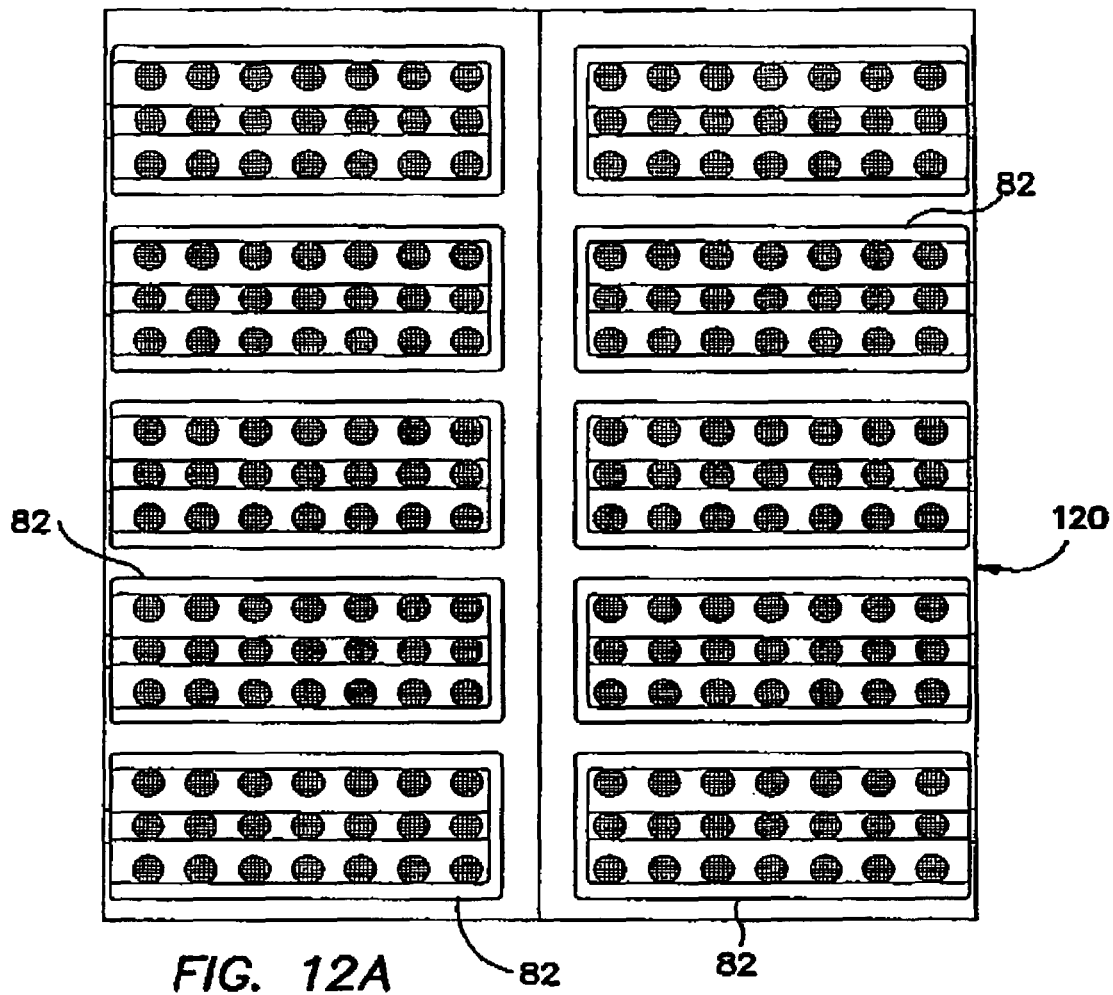
Figure 12B:
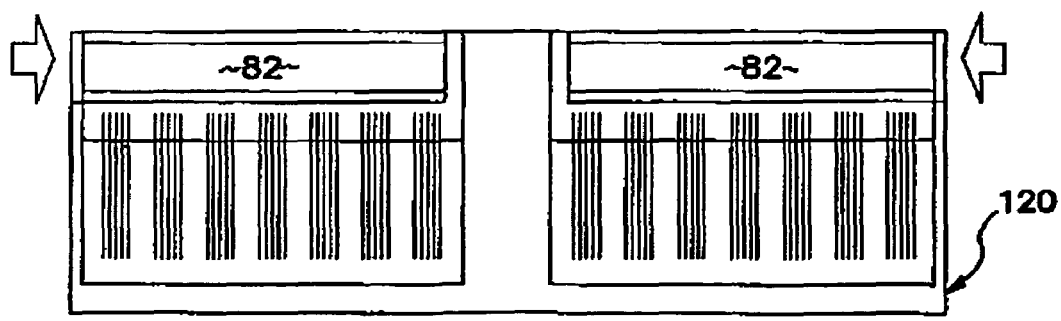

One embodiment, such as depicted in FIGS. 8, 9, 9A- and 9B, comprises a base 71, a removable cartridge 72 with rows of bristles 78, a moving arm 73 which may be transparent, a motor 74, a camera 75, rows of LEDs 76, and a tooth plaque remover 77. Another embodiment, which is depicted in FIGS. 10-, 11, 11A, 11B, 11C and 11D, comprises a base 81, a removable cartridge 82 with rows of bristles 88, a moving arm 83 which may be transparent, a motor 84, a camera 85, rows of LEDs 86, a tooth plaque remover 87, a first layer 89 of dentifrice which may comprise, for example, a first agent, and a second layer 90 of dentifrice which may comprise, for example, a second agent. FIGS. 12A and 12B depict a plurality of removable brushhead cartridges 82 (corresponding to elements 72 and 82 of FIGS. 8-9B and 10-11D, respectively) stored in complimentarily-shaped bins of a carriage 120.

Figure 12C:
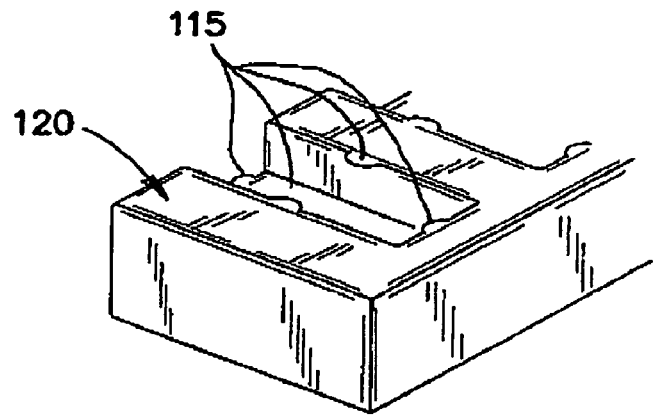
Figure 12D:
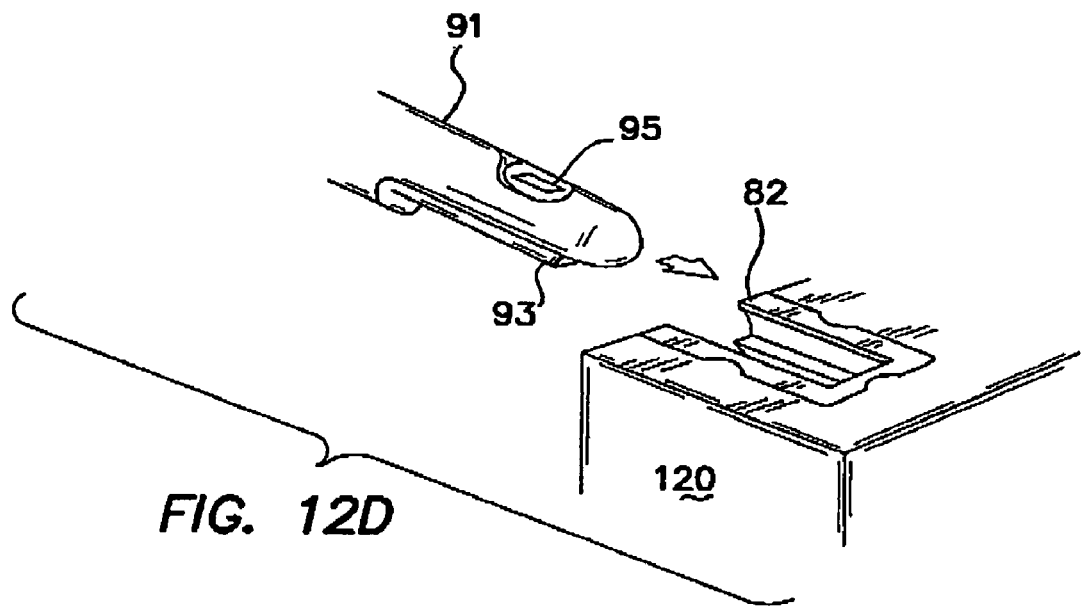

FIG. 12C shows a carriage 120 having complimentarily-shaved bins with holding bumps 115, and FIG. 12D shows a removable brushhead cartridge 82 held in one of the complimentarily-shaped bins of the carriage 120 of FIG. 12C by way of the holding bumps 115. A base 91 (corresponding to elements 71 and 81 of FIGS. 8-9B and 10-11D, respectively), having, among other things, a camera 95 (corresponding to elements 75 and 85 of FIGS. 8-9B and 10-11D, respectively) and a moving arm 93 (corresponding to elements 73 and 83 of FIGS. 8-9B and 10-11D, respectively) which may be transparent, can be contacted with the removable brushhead cartridge 82 for removal of the removable brushhead cartridge 82 from the complimentary-shaped bin of the carriage 120.

According to an illustrated embodiment of the present invention corresponding to FIGS. 12C and 12D, the base 91 can comprises a cartridge mounting groove for engaging corresponding structure of the removable brushbead cartridge 82 to facilitate coupling of the removable brushhead cartridge 82 to the base 81. Embodiments of such cartridge mounting grooves are exemplified with reference number 90 in FIGS. 13 and 16. Continuing with the discussion of FIGS. 12C and 12D, the cartridge mounting groove can further facilitate extraction of the removable brushhead cartridge 82 from the complimentarily-shaped bin after coupling of the base 91 to the removable brushhead cartridge 82 has been accomplished. In modified embodiments, other structures, such as may be known to those skilled in the art, may be implemented instead of or in addition to the described structures for coupling the removable brushhead cartridge 82 to the complimentarily-shaped bins.

In order to extract the removable brushhead cartridge 82 from the complimentarily-shaped bin, the base 91 may be inserted (e.g., slid) into the removable brushhead cartridge 82 to thereby couple the base 91 to the removable brushhead cartridge 82. Grooves (cf. 90 of FIGS. 13 and 16) on the base 91 may be inserted (e.g., slid) into contact with ridges (cf. 90 of FIGS. 13A. 14 and 15A) of the removable brushhead cartridge 82 to thereby couple the base 91 to the removable brushhead cartridge 82, followed by a lifting or pivoting movement of the base 91 away from the complimentary-shaped bin. This lifting or pivoting movement of the base 91 can generate a corresponding lifting or pivoting movement of the removable brushhead cartridge 82 for withdrawal of the removable brushhead cartridge 82 from the complimentarily-shaped bin. Typically the lifting or Pivoting movement of the removable brushhead cartridge 82 will need to be sufficient to effectuate a release of the removable brushhead cartridge 82 from the complimentary-shaped bin of the carriage 120. According to an aspect of the Present invention, the release may, in turn, generate a snap, corresponding, for example, to the removable brushhead cartridge 82 being freed from the holding bumps 115. In modified embodiments, other structures, such as shown in FIGS. 9A. 9B. 11A-11D and 13-16, or as may be known to those skilled in the art for facilitating removable couplings of structures, may be implemented instead of or in addition to the described structures for coupling the base 91 to the removable brushhead cartridge 82. Motor 74, 84; plaque remover 77, 87

With reference to FIG. 13, instead of a slide-in and lift/pivot movement, a region of the base 91 (e.g., a distal end) may be provided to initially contact a pivot region (e.g., a distal end) of the removable brushhead cartridge 92, followed by relative movement (e.g., pivoting) of the remainder (e.g., a proximal end) of the removable brushhead cartridge 92 into contact with the base 91. The base 91, may comprise, among other things, a cartridge mounting groove 90 which may be disposed on opposing sides of the base 91 as shown or all of the way around the distal end of the base 91, a transparent vibrating arm 93 and a LED array 96.

A view of structure corresponding in part to that of FIG. 13 is depicted in FIG. 13B. The base 91 of FIG. 13A may comprise, among other things, ridges 90 for facilitating snap-on engagement of the removable brushhead cartridge 92 or a plaque remover cartridge having a plaque remover 97, a vibrating arm 93 which may follow movement in the vertical and horizontal directions, a plurality of LEDs 94, and a built-in camera 95. The removable brushhead cartridge 92 may be coupled to the base 91 by way of parts of the removable brushhead cartridge 92 fitting over one or more cartridge mounting grooves and/or ridges 90 of the base 91, which coupling may be accompanied by a snap. Also, in FIG. 13A, a plaque remover cartridge, having a plaque remover 97 affixed thereto, may be coupled to the base 91 by way of parts of the plaque remover cartridge fitting over one or more cartridge mounting grooves and/or ridges 90 of the base 91, which coupling may be accompanied by a snap.

Another view of structure corresponding in part to that of FIG. 13 is depicted in FIG. 13B, showing engagement of vibrating arm 93 with complimentary structure of the removable brushhead cartridge 92, whereby movement of the vibrating arm 93 in an upward direction can result in bristles of the removable brushhead cartridge 92 pivoting outward away from one another or moving with an outward component, and whereby movement of the vibrating arm 93 in a downward direction can result in bristles of the removable brushhead cartridge 92 pivoting inward toward one another or moving with an inward component.

Figure 14:
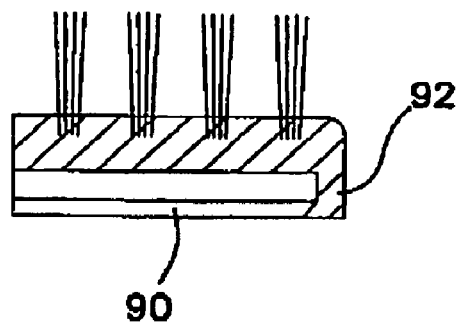
Figure 15A:
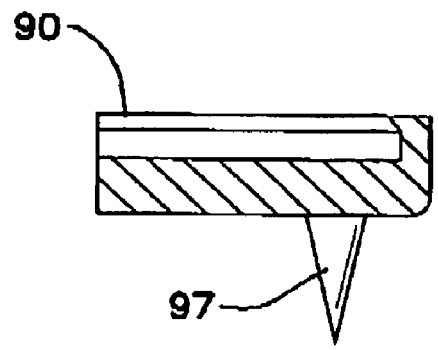

FIG. 14 is a side-elevation view of the removable brushhead cartridge 92 of FIG. 13A, showing one of the snap-on ridges 90. FIG. 15A is a side-elevation view of the plaque remover cartridge of FIG. 13A constructed to attach (e.g., snap-on) to ridges 90 of the base 91, and FIG. 15B is a side-elevation view of a plaque remover cartridge corresponding to that depicted in FIGS. 13A and 15A.

Figure 16:
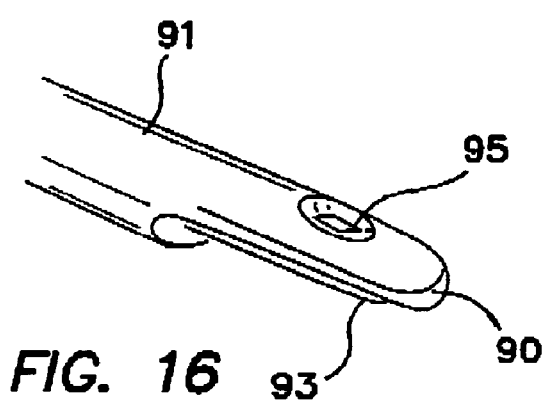
Figure 15B:
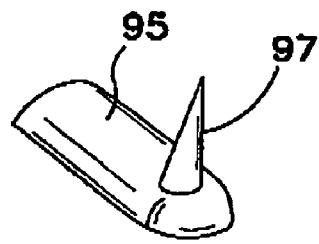

The perspective view of FIG. 15B elucidates a plaque remover cartridge corresponding to that of FIG. 15A in a snap-on plaque remover cartridge 95 implementation, wherein the plaque remover cartridge 95 may be transparent to facilitate operation of an underlying camera chip and lens assembly 95 such as depicted in FIG. 16. To couple the plaque remover cartridge 95 to the base 91, a region of the base 91 (e.g., a right side) may be provided to initially contact a corresponding region (e.g., a right side) of the plaque remover cartridge 95, followed by relative movement (e.g., pivoting) of the remainder (e.g., a left side) of the plaque remover cartridge 92 into contact with the corresponding structure (e.g., a left side) of the base 91, so that the snap-on ridges 90 (FIG. 15A) of the plaque remover cartridge 95 engage (e.g., snap onto) the cartridge mounting grooves 90 (FIG. 13) or ridges 90 (FIG. 13A) of the base 91.

Figure 17:
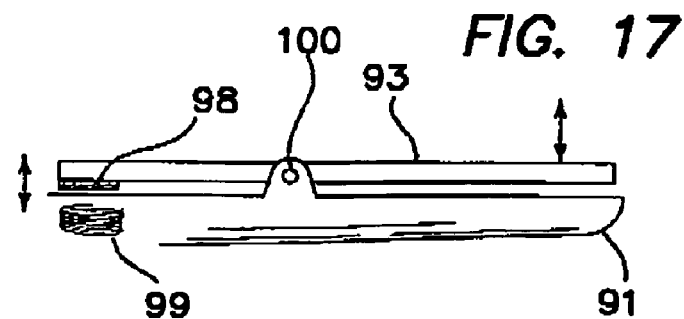

A side-elevation, partial cross-sectional view of the base 91 according to an up/down movement embodiment is depicted in FIG. 17, wherein the vibrating arm 93 is driven by a magnet 98 and an electrical coil 99 with alternating current to create movement of the vibrating arm (e.g., the transparent vibrating arm) 93, This movement of the vibrating arm 93 can comprise a pivoting or teetering movement about an axis 100, as indicated by the arrows in FIG. 17. When a removable brushhead cartridge 92 is coupled to the base 91, the un/down movement of the vibrating arm 93, resulting from the pivoting or teetering of the vibrating arm 93 about the axis 100, is transferred to the removable brushhead cartridge 92, This up/down movement may cause bristles of the removable brushhead cartridge as described and illustrated in connection with FIG. 13B.

Figure 18:
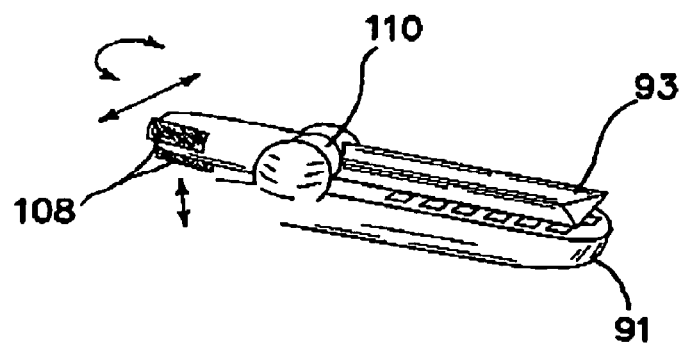

FIG. 18 shows a perspective view of a base 91 according to another embodiment of the present invention, having a structure somewhat similar in architecture and functionality to that described in relation to FIG. 17, wherein a vibrating arm 93 is driven by magnets 108 and corresponding electrical coils (not shown) to create movement of the vibrating arm 93. This movement of the vibrating arm 93 can comprise, as illustrated by the arrows in FIG. 17, any of a variety of directional movements of the vibrating arm 93 about the ball joint 110. For example, the movement may be in horizontal, vertical, and/or circular annular directions. The power to the magnets 108 from the electrical coils may be synchronized to isolate, combine or pattern the up/down, left/right and circular movements, When a removable brushhead cartridge 92 is coupled to the base 91, the movement of the vibrating arm 93 is transferred to the removable brushhead cartridge 92.

The platform, such as depicted in FIG. 13B comprising complementary structure for engaging the vibrating arm 93, can comprise a flexible area or divide in the form of, for example, a fold, bendable joint, perforated region, area of a flexible composition, or a complete or partial separation extending, for example, in a direction parallel with a longitudinal axis of the base structure. Thus, as a consequence of the flexible area, the base structure can be divided into a first (e.g., left) portion and a second (e.g., right) portion. According to modified embodiments, the base structure may be longitudinally divided into more than two portions. In an illustrated example, the platform is longitudinally divided in half into the first and second portions. The flexible area or divide may be provided in the form of, for example, a trench or crease, to facilitate flexing or bending of the base structure at or along, or in a vicinity of, the flexible area.

In accordance with certain implementations, movement forces can be applied to the base structure to cause the base structure to move, such as to pivot along the flexible area. Movement at or near the flexible area may comprise an oscillating movement, such as, for example, an oscillating movement along a direction having a vertical component, which vertical component can be defined along a direction parallel to at least some of the bristles. The movement may be implemented by linear motion of one or more arms coupled to, for example, the flexible area, and/or may be implemented by operation of one or more vibrating implements coupled to the cartridge (e.g., coupled to the base structure or, in an exemplary implementation, to the flexible areas).

In an embodiment wherein a flexible area is provided in the platform to define, for example, left and right portions, at least a part of an edge of each portion may be secured to a corresponding part of the toothbrush frame. The part or parts (e.g., an entire edge) of each portion that is secured to the toothbrush frame may comprise an edge that is located opposite to the flexible area. In such an embodiment, comprising, for instance, a flexible area extending lengthwise along a central part of the base structure and opposing edges (e.g., extending lengthwise as well) that are secured (e.g., movably, flexibly, or pivotally) to the toothbrush frame, flexing or bending of the base structure at the flexible area can facilitate a flapping or "butterfly" movement of the platform.

In certain embodiments the abrasive surfaces comprise bristles which are secured to the left and right portions in a manner to extend substantially normally from surfaces of the portions. Movement of the left and right portions of the platform can result in corresponding movements of textured surfaces of the platform. For example, the bristles may move in a sweeping motion along surfaces of the tooth.

In one embodiment, the toothbrush 1 can emit polychromatic electromagnetic radiation of a wavelength and an intensity for facilitating the removal of undesired substances from a target surface. Typical undesired substances can include, for example, bacteria, plaque, tartar, and calculus, all of which can contribute to, or are precursors of tooth decay. In other embodiments of the invention monochromatic electromagnetic radiation can be emitted to accomplish similar objectives.

The dentifrice is formulated in one embodiment to comprise photosensitive agents that assist in removing undesired substances from teeth, such as stains, bacteria, plaque, tartar, and calculus. The photosensitive agents can react to the emitted electromagnetic radiation of the toothbrush, for example, during brushing, to enhance removal of the undesired substances.

The removal enhancement provided by the dentifrice may be direct, such as when the photosensitive agent reacts to the electromagnetic radiation and, in turn, reacts with the undesired substance to remove it. Examples of materials that may comprise a photosensitive agent include peroxy compounds, salt compounds, anti-bacteria agents and anti-plaque agents. The salt compounds may or may not be dissolved in the dentifrice. The use of peroxide compounds, such as hydrogen peroxide and carbamide peroxide, in dentifrices is known in the art, as disclosed in U.S. Pat. No. 4,990,089 entitle METHOD AND MATERIAL FOR BRIGHTENING TEETH, which is incorporated herein by reference in its entirety. As a few further examples, the dentifrice may include one or more of the following compounds: peroxy compounds (such as hydrogen peroxide and/or carbamide peroxide), oxidoreductase agents (such as laccases, oxidases, and/or peroxidases), antibacterial agents (such as chlorhexidine digluconate, hexetidine, alexidine, quarternary ammonium and water-soluble sources of certain metal ions such as zinc, copper, silver, and stannous), anti-carries agents (such as fluoride), anti-plaque agents or plaque control activators, anti-tartar agents, desensitizing agents, etching agents (such as phosphoric acid), photosensitizers and photodynamic therapy photosensitizers, whitening agents, or pigments. The dentifrice may additionally or alternatively be conditioned (e.g., flavored) and comprise, in whole or in part and in any combination with the preceding ingredients, any of the ingredients as described in the above-referenced U.S. Pat. No. 6,350,123.

In accordance with the present invention, the electromagnetic radiation emitted by the toothbrush 1, for example, during brushing can enhance the whitening and cleaning of the teeth when used in combination with a dentifrice comprising a photosensitive agent. Other embodiments of the invention can comprise dentifrices used in connection with a photosensitive agent comprising, for example, a foaming agent. The foaming agent can generate foam, for example, in the presence of the electromagnetic radiation. The foam can operate as a carrier that delivers dentifrice to areas not reachable by the toothbrush cleaning surface, thus improving an overall cleaning and whitening of the teeth. The foaming agent may comprise a peroxy compound in one embodiment of the invention. In addition, when certain photosensitive agents are brought into contact with one or more undesired substances, the application of electromagnetic radiation having an appropriate wavelength and energy content can in certain instances render the substance or substances visible.

By way of example, one of the purposes of tooth brushing is to remove bacteria which have collected on tooth surfaces, frequently in pits and fissures in the tooth enamel. It is known that regardless of the care exercised and time spent in a brushing session, some of the bacteria deposits may not be dislodged and removed from the tooth surfaces. It is also known that there are chemical products, known as disclosing solutions, which can make any deposited bacteria visible. There are other photosensitive agents, which may be preferable to the conventional disclosing solutions, which will react with bacteria in such a manner as to render the bacteria visible in the presence of radiation having a certain wavelength or wavelengths.

When such a dentifrice is employed, the photosensitive agent can comprise a disclosing agent that renders any existing bacteria visible under the radiation produced by the light-emitting device 14 by changing the color of the disclosing agent. The disclosing agent has an affinity for undesired substances, such as bacteria and/or plaque, resulting in the disclosing agent being concentrated about the undesired substances relative to other areas on the target surface. As a result, the radiated, disclosing agent announces locations of undesired substances on the teeth surface, so that brushing can be continued until the user observes that all bacteria have been removed from all visible tooth surfaces. While it would be more difficult to carry out this procedure on lingual tooth surfaces, this would be possible, if brushing were carried out while viewing those surfaces with a mirror. The dentifrices of modified embodiments of the invention may additionally or alternatively visually announce plaque and/or other undesired substances during brushing as well.

According to one exemplary embodiment of the invention, the chemical product can consists essentially of or contains Black Shade No. 4625, which can be obtained by Crompton & Knowles, Ingredient Technology Division, of Reading, Pa. In this embodiment, the radiation source can produce radiation at a wavelength, or wavelengths, of between 0.8 mm and 1 mm. As presently embodied, the radiation source can produce polychromatic electromagnetic radiation of wavelengths ranging from 0.8 mm to 1 mm. In a modified embodiment of the invention, the radiation source can produce polychromatic electromagnetic radiation of wavelengths comprising at least a portion of the different wavelengths in the 0.8 mm to 1 mm range. In still another modified embodiment, the radiation source can produce electromagnetic radiation of a single wavelength in the 0.8 mm to 1 mm range. The radiation source may comprise, for example, a Nd:YAG laser.

The radiation source can be adjusted to emit radiation at an energy level selected on the basis of the expected concentration of the Black Shade No. 4625 in the material to be treated. The Black Shade No. 4625 will stain, for example, cariogenic bacteria or *streptococcus faecalis* black so that this bacteria, or any other substance absorbing Black Shade No. 4625, will readily absorb the laser radiation. As an alternative to the Black Shade No. 4625 in the example, any other substance for staining the bacteria, for example, black can be used. Other photosensitive substances may be used in addition to, or as an alternative to, black. Agents comprising oranges, reds, browns, yellows, greens, blues, etc., supplied, for example, by Crompton & Knowles may be selected, along with radiation sources having corresponding wavelengths. According to one specific embodiment, the chemical product is sudan red as a vital stain and the radiation source is an argon laser.

The radiation energy density can be made sufficiently high to directly vaporize the stained substance. For example, in the case where *streptococcus faecalis* is stained with Black Shade No. 4625 and irradiated by an Nd:YAG laser, this effect can be achieved with an energy density on the order of 10 $J/cm^2$.

To improve efficiency in accordance with the present invention, the dentifrice can be configured to transmit an optimum amount of electromagnetic radiation therethrough. In an embodiment of the invention, an optimum amount of transmission through the dentifrice can comprise transmitting electromagnetic radiation at wavelengths and intensities thereof to facilitate reaction of the photosensitive agent and substantially no additional electromagnetic radiation beyond that. Typical embodiments of the invention have the photosensitive agents dispersed throughout the dentifrice. During brushing, the dentifrice is dispersed in varying thicknesses over the target surface, which can comprise the teeth and gums. To be effective, the electromagnetic radiation should penetrate through the dentifrice's varying thickness, so that significant portions of the photosensitive agent throughout the varying thicknesses are irradiated and react. For this to occur, the dentifrice in certain embodiments transmits the radiation through the varying thicknesses, thereby enabling the significant portions of the dispersed photosensitive agent throughout the dentifrice to substantially absorb the radiation and react.

In modified embodiments of the invention, the dentifrice is clear, translucent, tinted, opaque, or a combination thereof. The term "clear" shall be understood to mean visually colorless and transparent. In one embodiment of the invention, the dentifrice is a clear gel comprising at least about 1.5 percent hydrogen peroxide and a clear base. In an exemplary embodiment, the base comprises water, hydrogen peroxide, poloxamer 407, glycerine, flavor and sodium saccharin. In another exemplary embodiment, the base comprises fluoride, hydrogen peroxide, and hydrated silica. The clear gel can optimize or maximize transmission of radiation therethrough, to thereby maximize an interaction of the clear gel with the radiation throughout the thickness of the clear gel.

In further modified embodiments of the invention, the container may comprise compartments which hold a first portion of the dentifrice in one compartment and a second portion of the dentifrice in the other compartment (not shown). The separation of the dentifrice portions may prevent components in the separate portions from reacting prior to use. For example, a first portion comprising baking soda can be separated from a second portion comprising hydrogen peroxide.

In accordance with one embodiment, the active ingredient or ingredients of the dentifrice can be engineered to remain relatively stable until the dentifrice is disposed on the tooth. In an embodiment where the dentifrice comprises peroxide, for example, the dentifrice can be engineered to hold the peroxide in a relatively stable condition both while in the tube and while initially on the toothbrush.

In addition to engineering the dentifrice to remain stable until placed on the tooth and agitated, a method of the invention can comprise a step of instructing the user to leave the source of the toothbrush in an off mode until the toothbrush and dentifrice are placed on the teeth. The user follows the instructions and inserts the toothbrush, with the dentifrice thereon and with the source in an off mode, into the mouth and Onto the teeth of the user. Subsequently, the user places the source into an on mode to thereby initiate the emission of radiation from the toothbrush into the dentifrice. The user can then move the bristles of the toothbrush on the teeth to agitate and further activate the active ingredient or ingredients of the dentifrice. In selected embodiments, the mere placement of the dentifrice on a tooth, with or without agitation, initiates activation of the ingredient or ingredients of the dentifrice. For example, a stain comprising iron, disposed on a tooth, can help to activate the peroxide of a dentifrice when the dentifrice is placed into contact with the stain on the tooth. In this example, the additional irradiation of the dentifrice can enhance the activation. In other embodiments of the above examples, the bristles of the toothbrush are placed only into close proximity with the teeth.

In still other embodiments of the invention, the dentifrice may comprise abrasives. The abrasives may be visible, an example of which is disclosed in U.S. Pat. No. 3,935,306, entitled TOOTHPASTE FORMULATIONS, which is incorporated herein by reference. The abrasives may be clear, an example of which is disclosed in U.S. Pat. No. 3,864,470, entitled VISUALLY CLEAR TOOTHPASTE CONTAINING SYNTHETIC PRECIPITATED HYDRATED SILICA, which is incorporated herein by reference. Clear abrasive particles may enhance the transmissibility of the dentifrice, as compared to opaque abrasive particles.

In a particular embodiment of the invention, the electromagnetic radiation emitted from the toothbrush 1 is substantially free of ultraviolet radiation. Ultraviolet radiation is a relatively high energy wavelength range, compared to visible and infrared wavelengths. Under some circumstances, directing ultraviolet radiation into the mouth may result in cellular damage. Further, as the ultraviolet radiation is higher energy, the toothbrush 1 may consume less energy during operation as it does not emit the higher energy ultraviolet wavelengths.

In certain embodiments of the invention, the dentifrice and the toothbrush 1 can be tuned to be efficient together or to provide a desired effect. For instance, the dentifrice can be formulated with a photosensitive agent and then tested, using techniques known to those skilled in the art, to determine wide-range reactive electromagnetic radiation wavelengths that cause the photosensitive agents to react. The toothbrush 1 can then be designed such that it emits at least a portion of the wide-range electromagnetic radiation wavelengths. Other embodiments of the invention may comprise a toothbrush that emits electromagnetic radiation wavelengths consisting essentially of non-ultraviolet radiation, or, consisting essentially of wavelengths within a range of 300 to 750 nanometers.

Other embodiments of the invention can comprise a toothbrush that emits electromagnetic radiation within the infrared or near-infrared region. Compounds can be selected to react with this light exclusively or in addition to other wavelengths. The radiation from the source may comprise a single wavelength in the infrared or near-infrared region, or may comprise a plurality of wavelengths in the infrared or near-infrared region. In one embodiment, the infrared or near-infrared region is selected to comprise a range of wavelengths from about 700 nm to about 990 nm. In another embodiment, the infrared or near-infrared region is selected to comprise visible light, as well, for a combined range of wavelengths from about 300 nm to about 990 nm, or to about 1 mm.

Other embodiments of the invention may comprise determining a narrow-range of electromagnetic radiation wavelengths, wherein the photosensitive agent has a relatively high reaction rate when exposed to the narrow-range reactive electromagnetic radiation wavelengths compared to an average reaction rate when the photosensitive agent is exposed to the wide-range reactive electromagnetic radiation wavelengths. The toothbrush 1 can be designed to provide electromagnetic radiation, which is substantially in the narrow-range reactive electromagnetic radiation wavelengths.

What is claimed is:

1. A tissue treatment device, comprising:
   a handle suitable to be gripped by a hand of a user;
   an electric movement mechanism;
   first and second activated textured surfaces arranged on the device in row, with first and second bristles arranged on the device in rows configured to be activated by the electric movement mechanism to apply one or more of agitation and cleaning forces onto a tissue site, and with a dentifrice of first and second layers and respective first and second agents having first and second sensitivities to first and second different wavelengths, the second bristles having greater heights than the first bristles in order to direct light through the first layer into the second layer; and
   first and second electromagnetic energy outputs for respectively producing said first and second wavelengths disposed in a vicinity of each of the rows and configured to be activated to direct light into each of the plurality of activated textured surfaces.

2. The tissue treatment device as set forth in claim 1, the tissue treatment device comprising a cartridge surface, wherein the bristles terminate at and are attached to the cartridge surface, which is constructed to be readily, removably and interchangeably coupled to a complimentary surface of the tissue treatment device and to a complimentary area of a storage cartridge holder, the storage cartridge holder being constructed to removably hold a plurality of cartridge surfaces in orientations that are substantially identical to one another.

3. The tissue treatment device as set forth in claim 2, wherein:
   the cartridge surfaces are planar surfaces, and
   the storage cartridge holder holds the cartridge surfaces so that all of the planar surfaces are parallel to one another.

4. The tissue treatment device as set forth in claim 3, wherein the cartridge surfaces have rectangular perimeters and the storage cartridge holder has a rectangular perimeter.

5. The tissue treatment device as set forth in claim 1, wherein the tissue treatment device is a toothbrush.

6. The tissue treatment device as set forth in claim 5, wherein at least one bristle of a row can be activated to oscillate in a direction substantially perpendicular to the row in which it is disposed.

7. The tissue treatment device as set forth in claim 5, wherein at least one bristle of a row can be activated to rotate.

8. The tissue treatment device as set forth in claim 5, wherein at least one bristle of a row can be activated to oscillate in a direction substantially parallel to the row in which it is disposed.

9. The tissue treatment device as set forth in claim 8, wherein at least one electromagnetic energy output is positioned in each row to provide constant irradiation of at least a portion of that row as different parts of the at least one bristle in that row move over the electromagnetic energy output.

10. The tissue treatment device as set forth in claim 8, wherein:
the at least one bristle comprises a plurality of bristles; and
at least one electromagnetic energy output is positioned in each row to constantly irradiate a corresponding part of that row so that electromagnetic energy from the electromagnetic energy output is directed into the part even as different bristles in that row are irradiated by the electromagnetic energy output during each cycle of oscillation of the bristles in that row.

11. The tissue treatment device as set forth in claim 10, wherein the at least one electromagnetic energy output in each row comprises a plurality of electromagnetic energy outputs.

12. The tissue treatment device as set forth in claim 8, wherein the at least one bristle in each row comprises a plurality of bristles.

13. The tissue treatment device as set forth in claim 12, wherein each electromagnetic energy output is disposed under a corresponding row.

14. The tissue treatment device as set forth in claim 8, wherein the bristles and the electromagnetic energy outputs are configured to be activated simultaneously.

15. The tissue treatment device as set forth in claim 8, wherein the electromagnetic energy outputs comprise LEDs.

16. The tissue treatment device as set forth in claim 1, wherein:
the at least one bristle in each row comprises a plurality of bristles;
each electromagnetic energy output is disposed under a corresponding row;
the bristles and the electromagnetic energy outputs are configured to be activated simultaneously; and
the electromagnetic energy outputs comprise LEDs.

17. The tissue treatment device as set forth in claim 1, and further comprising:
a visualization device suitable for communicating image data from a distal end of the treatment to a display; and
a plaque remover implement.

18. The tissue treatment device as set forth in claim 17, wherein the visualization device comprises an intraoral video camera constructed with one or more light sources having wavelengths and associated circuitry designed to elucidate or visually differentiate one or more tissue conditions.

19. The tissue treatment device as set forth in claim 18, the visualization device and plaque remover implement enabling a user to identify treatment conditions and, in real time, to use the plaque remover implement to treat the condition.

20. The tissue treatment device as set forth in claim 19, and further comprising irrigation and suction structures.

21. The tissue treatment device as set forth in claim 1, wherein the dentifrice is arranged so that the second layer is positioned furthest away from the electromagnetic energy outputs.

22. A tissue treatment device, comprising:
a handle suitable to be gripped by a hand of a user;
an electric movement mechanism;
a plurality of activated textured surfaces arranged on the device in rows, configured to be activated by the electric movement mechanism to apply one or more of agitation and cleaning forces onto a tissue site;
first and second electromagnetic energy outputs with different wavelengths, disposed in a vicinity of each of the rows and configured to be activated to direct light into each of the plurality of activated textured surfaces; and
a dentifrice disposed on the activated textured surfaces with a first layer comprising a first agent that is more sensitive to wavelengths from the first electromagnetic energy output and with a second layer comprising a second agent that is more sensitive to wavelengths from the second electromagnetic energy output, wherein the surfaces comprise bristles of a first height and bristles of a second height greater than the first height to direct electromagnetic energy through the first layer and into the second layer.

23. The tissue treatment device as set forth in claim 22, wherein the bristles of the second height are configured to output a greater power.

24. The tissue treatment device as set forth in claim 22, wherein distal ends of the bristles of the second height extend at least partially through the first layer.

25. A tissue treatment device, comprising:
a handle suitable to be gripped by a hand of a user;
a plurality of activated textured surfaces arranged on the device in rows and configured to be activated to apply one or more of agitation and cleaning forces onto a tissue site, the plurality of activated textured surfaces comprising first activated textured surfaces of a first height and further comprising second activated textured surfaces of a second, greater height; and
at least one electromagnetic energy output disposed in a vicinity of each of the rows and configured to be activated to direct a first treatment energy into the first activated textured surfaces and to direct a second treatment energy, differing in at least one characteristic from the first treatment energy, into the second activated textured surfaces.

26. The tissue treatment device as set forth in claim 25, wherein the plurality of activated textured surfaces comprises a plurality of bristles arranged on the device in rows and configured to be activated to apply one or more of agitation and cleaning forces onto a tissue site, whereby the plurality of bristles is arranged into bristles of the first height and bristles of the second height.

27. The tissue treatment device as set forth in claim 26, wherein the second activated textured surfaces are configured to output a greater power.

28. The tissue treatment device as set forth in claim 25, wherein the second activated textured surfaces are configured to output a greater power.

29. The tissue treatment device as set forth in claim 25, and further comprising a dentifrice disposed on the activated textured surfaces, wherein:
the at least one electromagnetic energy output comprises a first electromagnetic energy output and a second electromagnetic energy output having a wavelength different from the first electromagnetic energy output; and the dentifrice includes a first layer with a first agent that is more sensitive to wavelengths from the first electromagnetic energy output and a second layer with a second agent that is more sensitive to wavelengths from the second electromagnetic energy output.

30. The tissue treatment device as set forth in claim 29, wherein the second activated textured surfaces are configured to output a greater power and the dentifrice is arranged so that the second layer is positioned furthest away from the electromagnetic energy outputs.

31. The tissue treatment device as set forth in claim 30, wherein distal ends of the second activated textured surfaces extend at least partially through the a first layer.

32. The tissue treatment device as set forth in claim 31, wherein the activated textured surfaces comprise bristles arranged into bristles of the first height and bristles of the second height.

33. The tissue treatment device as set forth in claim 25, wherein the activated textured surfaces comprise bristles arranged into:
   bristles of the first height; and
   bristles of the second height that are configured to output electromagnetic energy having a greater power than that emitted from the bristles of the first height and having a wavelength different from that emitted from the bristles of the first height.

34. The tissue treatment device as set forth in claim 25, wherein a dentifrice is disposed on at least a portion of the activated textured surfaces, which include (a) first bristles of the first height and (b) second bristles of the second height that are configured to output electromagnetic energy having a power greater than and a wavelength different from that emitted from the first bristles.

* * * * *

UNITED STATES PATENT AND TRADEMARK OFFICE
CERTIFICATE OF CORRECTION

| | | |
|---|---|---|
| PATENT NO. | : 7,467,946 B2 | Page 1 of 1 |
| APPLICATION NO. | : 11/438091 | |
| DATED | : December 23, 2008 | |
| INVENTOR(S) | : Ioana M. Rizoiu, Jeffrey W. Jones and Dmitri Boutoussov | |

It is certified that error appears in the above-identified patent and that said Letters Patent is hereby corrected as shown below:

Col. 30, lines 29-47;
Claim 1 on page 26 of the above-referenced patent has been corrected to read as follows:

1. A tissue treatment device, comprising:
a handle suitable to be gripped by a hand of a user;
an electric movement mechanism;
first and second activated textured surfaces arranged on the device in rows, with first and second bristles arranged on the device in rows configured to be activated by the electric movement mechanism to apply one or more of agitation and cleaning forces onto a tissue site, and with a dentifrice of first and second layers and respective first and second agents having first and second sensitivities to first and second different wavelengths,
the second bristles having greater heights than the first bristles in order to direct light through the first layer into the second layer; and
first and second electromagnetic energy outputs for respectively producing said first and second wavelengths disposed in a vicinity of each of the rows and configured to be activated to direct light into each of the plurality of activated textured surfaces.

Signed and Sealed this
Fourth Day of January, 2011

David J. Kappos
*Director of the United States Patent and Trademark Office*